United States Patent
Erdağ et al.

(10) Patent No.: US 9,193,792 B2
(45) Date of Patent: Nov. 24, 2015

(54) RECOMBINANT ANTIBODY STRUCTURES BINDING TO AND BLOCKING THE ACTIVITY OF VASCULAR ENDOTHELIAL GROWTH FACTOR 2 (VEGFR—2/KDR)

(75) Inventors: Berrin Erdağ, Gebze (TK); Bertan Koray Balcioğlu, Gebze (TK); Aylin Ozdemir Bahadir, Gebze (TK); Aydin Bahar, Gebze (TK); Kemal Baysal, Gebze (TK); Müge Serhatli, Gebze (TK); Omer Kaçar, Gebze (TK); Türker Kiliç, Istanbul (TK); Emel Akgün, Istanbul (TK); Abdulkadir Özkan, Istanbul (TK)

(73) Assignee: TUBITAK, Ankara (TR)

( * ) Notice: Subject to any disclaimer, the term of this patent is extended or adjusted under 35 U.S.C. 154(b) by 0 days.

(21) Appl. No.: 13/808,295

(22) PCT Filed: Jul. 7, 2010

(86) PCT No.: PCT/IB2010/053109
§ 371 (c)(1),
(2), (4) Date: Mar. 9, 2013

(87) PCT Pub. No.: WO2012/004631
PCT Pub. Date: Jan. 12, 2012

(65) Prior Publication Data
US 2014/0199301 A1   Jul. 17, 2014

(51) Int. Cl.
C07K 16/28 (2006.01)
A61K 39/00 (2006.01)

(52) U.S. Cl.
CPC ........ *C07K 16/2863* (2013.01); *A61K 2039/505* (2013.01); *C07K 2317/622* (2013.01); *C07K 2317/73* (2013.01)

(58) Field of Classification Search
CPC ..................... C07K 16/2863; C07K 2317/622
See application file for complete search history.

(56) References Cited

U.S. PATENT DOCUMENTS

2005/0214860 A1* 9/2005 Zhu et al. ........................ 435/7.1

OTHER PUBLICATIONS

Ward et al. (Nature 341:544-546 (1989)).*
De Pascalis et al. The Journal of Immunology (2002) 169, 3076-3084.*
Casset et al. ((2003) BBRC 307, 198-205).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Padlan et al. (PNAS 1989, 86:5938-5942).*
Lamminmaki et al. (JBC 2001,276:36687-36694).*

* cited by examiner

*Primary Examiner* — Daniel C Gamett
(74) *Attorney, Agent, or Firm* — Brinks Gilson & Lione

(57) ABSTRACT

Phage displayed recombinant antibody library was developed and the library was screened against VEGFR-2. After screening and ELISA experiments two recombinant antibodies showing binding properties to VEGFR-2 was obtained. The difference of the two recombinant antibodies to the recombinant antibodies already developed was demonstrated by DNA sequence analysis. The inhibition effect of the two recombinant antibodies on endothelial cell proliferation was demonstrated with cell assays. Thus these recombinant antibodies might be used as VEGF related angiogenesis inhibitors.

10 Claims, 12 Drawing Sheets

Agarose gel electrophoresis image of variable light and heavy chains of the scFv produced against KDR.

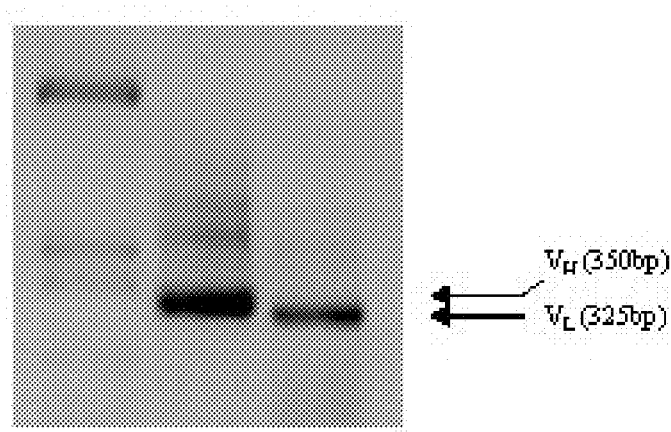

Figure 1: Agarose gel electrophoresis image of variable light and heavy chains of the scFv produced against KDR.

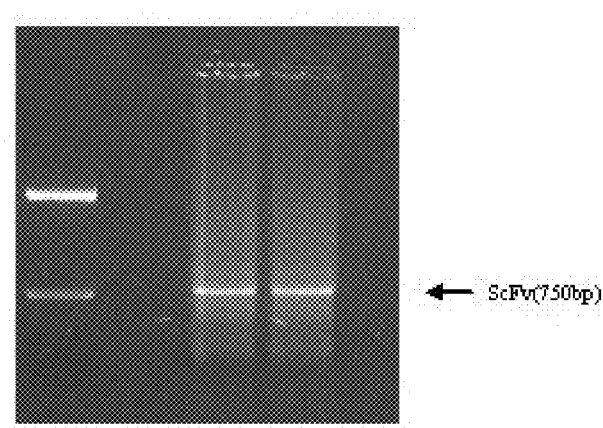

Figure 2: Agarose gel electrophoresis image of single chain variable fragment produced from the ligation of variable light and heavy chains with a linker coding for $(Gly_4Ser)_3$.

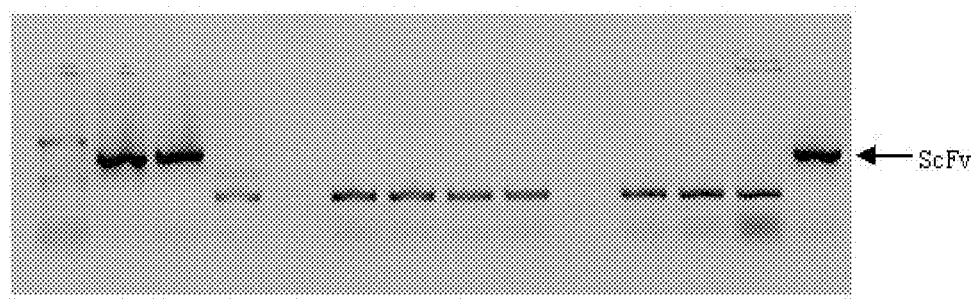

FIGURE 3: Colony PCR results of randomly selected colonies obtained from the transformation *E. coli* TG1 bacteria with the ligation product of KDR1.3 scFv.

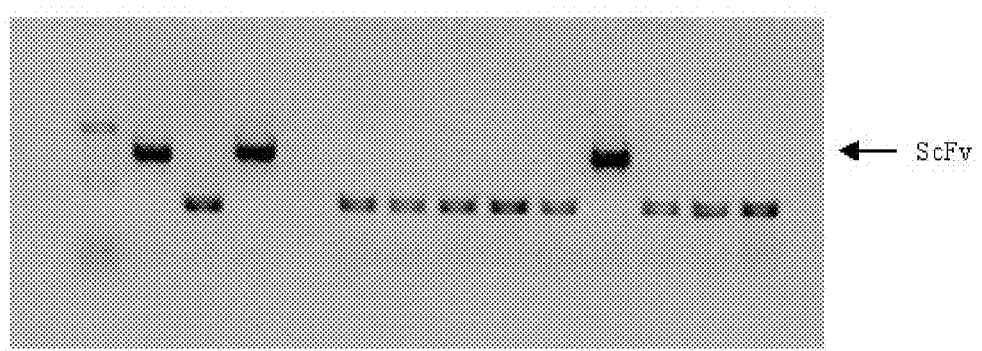
FIGURE 4: Colony PCR results of randomly selected colonies obtained from the transformation *E. coli* TG1 bacteria with the ligation product of KDR2.6 scFv.
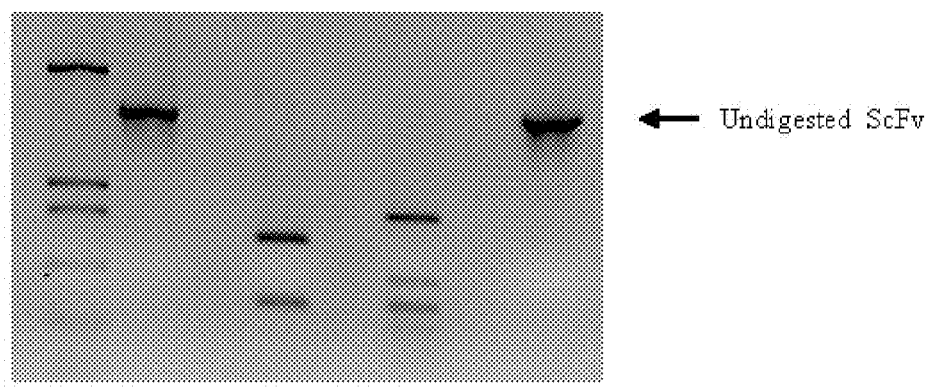
FIGURE 5: BstnI digestion profile of KDR1.3 and KDR2.6 scFv clones.

```
  L   L   G   E   V   I   M   K   Y   L   L   P   T   A   A   A   G   L   L   L   A   A
 ctt tta gga gaa gtc ata atg aaa tac cta ttg cct acg gca gcc gct gga ttg tta tta ctc gcg gcc FR1
  Q   P   A   M   A   Q   V   K   L   Q   Q   S   G   P   S   L   V   K   P   S   Q   T   L
 cag ccg gcc atg gcc cag gtg aag ctg cag cag tca gga cct agc ctc gtg aaa cct tct cag act ctg CDR1
  S   L   T   C   S   V   T   G   D   S   I   T   S   G   Y   W   N   W   I   R   K   F   P
 tcc ctc acc tgt tct gtc act ggc gac tcc atc acc agt ggt tac tgg aac tgg atc cgg aaa ttc cca FR2                                                    CDR2
  G   H   K   L   E   Y   M   G   Y   I   S   Y   S   G   S   T   Y   Y   N   P   S   L   K
 ggg cat aaa ctt gag tac atg ggg tac ata agc tac agt ggt agc act tat tat aat cca tct ctc aaa FR3
  S   R   I   S   I   T   R   D   T   S   K   N   Q   F   F   L   Q   L   N   S   V   T   T
 agt cga atc tct atc act cga gac aca tcc aag aac cag ttc ttc ctg cag ttg aat tct gtg act act CDR3
  E   D   T   A   T   Y   Y   C   A   R   Y   G   G   N   Y   F   D   Y   W   G   Q   G   T
 gag gac aca gcc aca Tat tac tgt gca aga tat ggt ggt aac tac ttt gac tac tgg ggc caa ggg acc T   V   T   V   S   S   G   G   G   G   S   G   G   G   G   S   G   G   G   G   A   D   I
 acg gtc acc gtc tcc tca ggt gga ggc ggt tca ggc gga ggt ggc tct ggc ggt ggc gga gcg gac atc FR1
  E   L   T   Q   S   P   A   I   M   S   A   S   P   G   E   K   V   T   M   T   C   S   A
 gag ctc act cag tct cca gca atc atg tct gca tct cca ggg gag aag gtc acc atg acc tgc agt gcc CDR1                                                 FR2
  S   S   S   V   S   Y   M   H   W   Y   Q   Q   K   S   G   T   S   P   K   R   W   I   Y
 agc tca agt gta agt tac atg cac tgg tac cag cag aag tca ggc acc tcc ccc aaa aga tgg att tat CDR2                                                              FR3
  D   T   S   K   L   A   S   G   V   P   A   R   F   S   G   S   G   S   G   T   S   Y   S
 gac aca tcc aaa ctg gct tct gga gtc cct gct cgc ttc agt ggc agt ggg tct ggg acc tct tac tct CDR3
  L   T   I   S   S   M   E   A   E   D   V   A   T   Y   Y   C   F   Q   G   S   G   Y   P
 ctc aca atc agc agc atg gag gct gaa gat gtt gcc act tat tac tgt ttt cag ggg agt ggg tac cca F   G   A   R   T   K   L   E   L   K   R   A   A   A   H   H   H   H   H   H   Q
 ctc acg ttc ggt gct agg acc Aag ctg gag ctg aaa cgg gcg gcc gca cat cac cat cat cat cac cag A   A   E   Q   K   L   I   S   E   E   D   L
 gcc gca gaa caa aaa ctc atc tca gaa gag gat ctg
```

FIGURE 6: DNA sequence of KDR1.3 scFv and the emplacement of CDR region predicted from IMGT web site.

```
                                                    FR1
  Q   V   K   L   Q   E   S   G   P   E   L   E   K   P   G   A   S   V   K   I   S   C   K   A
cag gtc aaa ctg cag gag tct gga cct gag ctg gag aag cct ggc gct tca gtg aag att tcc tgc aag gct FR2
  S   G   Y   A   F   I   G   Y   N   M   N   W   V   K   S   N   E   K   S   L   E   W   I
tcc ggt tac gca ttc att ggc tac aac atg aac tgg gtg aag agc aat gaa aag agc ctt gag tgg att CDR2
  G   N   I   D   P   Y   Y   C   G   T   S   Y   N   Q   K   F   K   G   K   A   T   M   T   V
gga aat att gat cct tac tat tgt ggg act agc tac aac cag aag ttc aag ggc aag gcc aca atg act gta FR3
  D   E   S   S   T   A   F   M   Q   L   K   S   L   T   S   E   D   S   A   V   Y   Y   C
gac gaa tcc tcc agc aca gcc ttc atg cag ctc aag agc ctg aca tct gag gac tct gca gtc tat tac tgt CDR3
  A   R   G   T   M   I   T   T   S   Y   A   M   D   Y   W   G   Q   G   T   T   V   T   V   S
gca agg ggg act atg att acg acg tcc tat gct atg gac tac tgg ggc caa ggg acc acg gtc acc gtc tcc S   S   G   G   G   S   G   G   G   G   S   G   G   G   G   S   D   I   E   L   T   Q   S   P
tca agt gga ggc ggt tca ggc gga ggt ggc tct ggt ggt ggc gga tcg gac atc gag ctc act cag tct cca
                        FR1
  A   I   L   S   A   S   P   G   E   K   V   T   M   T   C   R   A   S   S   S   V   S   Y   M
gca atc ctg tct gcg tct cca ggg gag aag gtc aca atg act tgc agg gcc agc tca agt gta agt tac atg FR2                                          CDR2
  H   W   Y   Q   Q   K   P   G   S   S   P   K   P   W   I   Y   A   T   S   N   L   A   S   G
cac tgg tac cag cag aag cca gga tcc tcc ccc aaa ccc tgg att tat gcc aca tcc aac ctg gct tct gga FR3
  V   P   A   R   F   S   G   S   G   S   G   T   S   Y   S   L   T   I   S   R   V   E   A   E
gtc cct gct cgc ttc agt ggc agt ggg tct ggg acc tct tac tct ctc aca atc agc aga gtg gag gct gaa CDR3
  D   A   A   T   Y   S   C   Q   Q   W   S   S   N   L   L   T   F   G   A   G   T   K   L   E
gat gct gcc act tat tcc tgc cag cag tgg agt agt aac ctg ctc acg ttc ggt gct ggg acc aag ctg gaa I   K   R   A   A   H   H   H   H   H   H   Q   A   A   E   Q   K   L   I   S   E   E   D
ata aaa cgg gcg gcc gca cat cac cat cac cat cac cag gcc gca gaa caa aaa ctc atc tca gaa gag gat L   N   G   A   A
ctg aat ggg gcc gca
```

FIGURE 7: DNA sequence of KDR2.6 scFv and the emplacement of CDR regions predicted from IMGT web site.

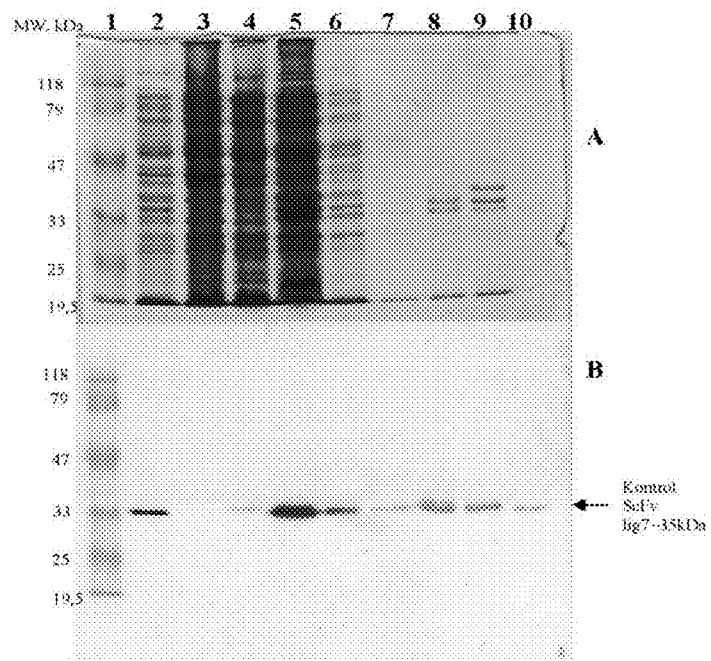
Figure 8: SDS-PAGE and western blot analysis results of the KDR 1.3 recombinant antibody
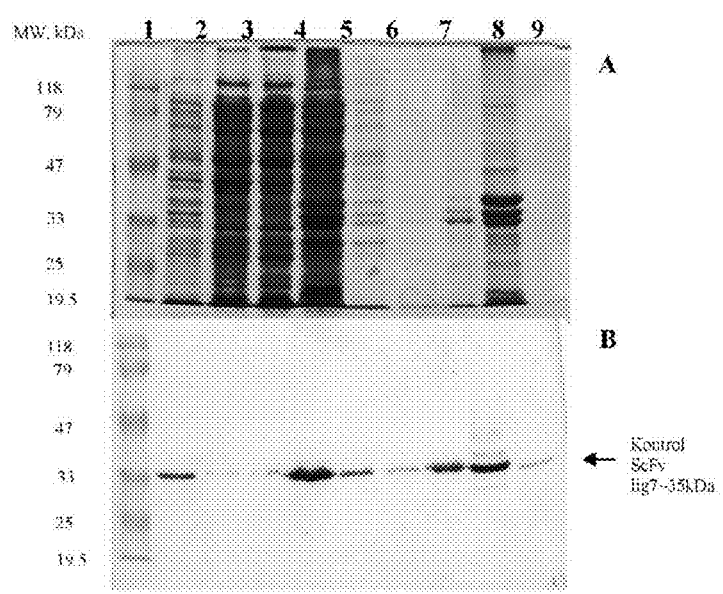
FIGURE 9: SDS-PAGE and western blot analysis results of the KDR 2.6 recombinant antibody.

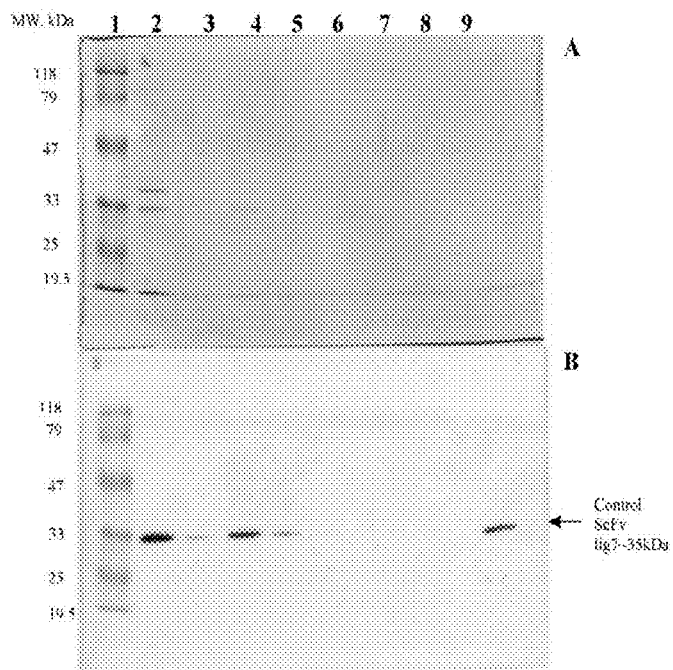
FIGURE 10: SDS-PAGE and western blot analysis results of TALON affinity colon purified KDR 1.3 scFv
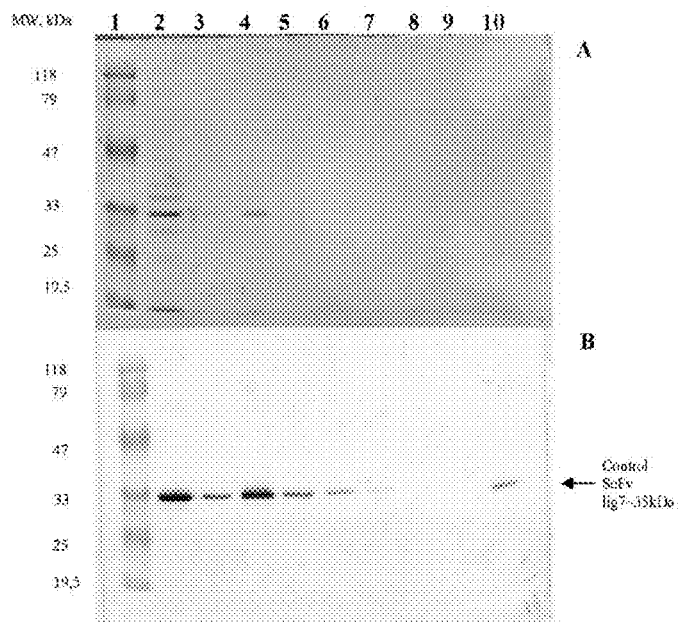
FIGURE 11: SDS-PAGE and western blot analysis results of TALON affinity colon purified KDR 2.6 scFv.

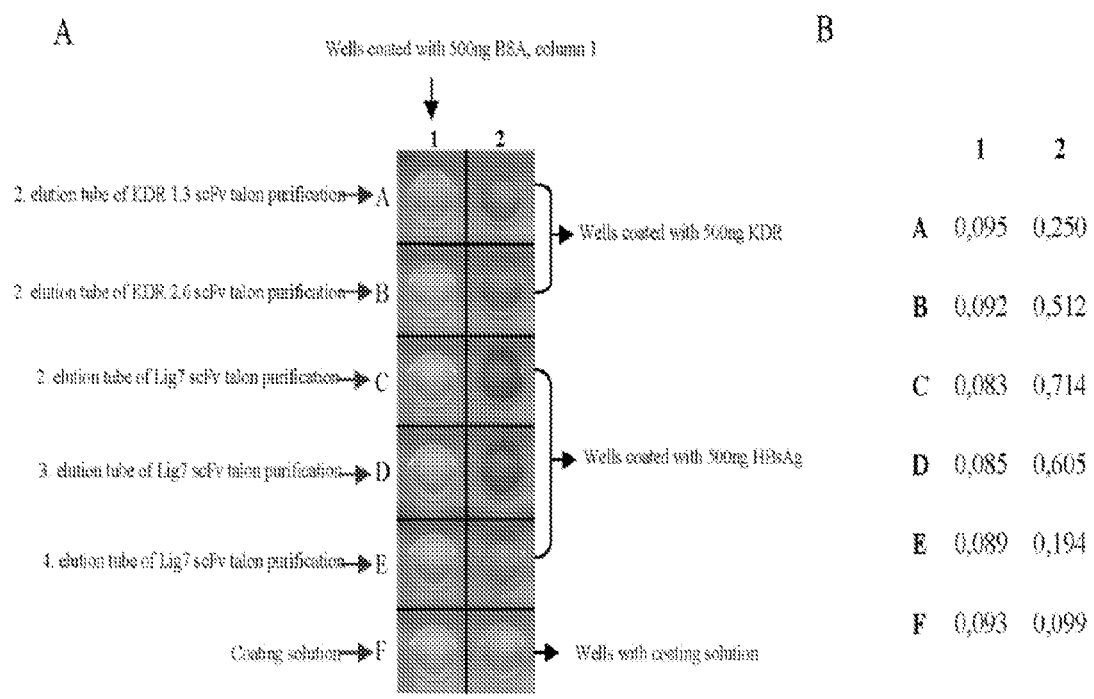
FIGURE 12: ELISA results of TALON purified KDR 1.3, 2.6 and Lig7 (control) scFv.

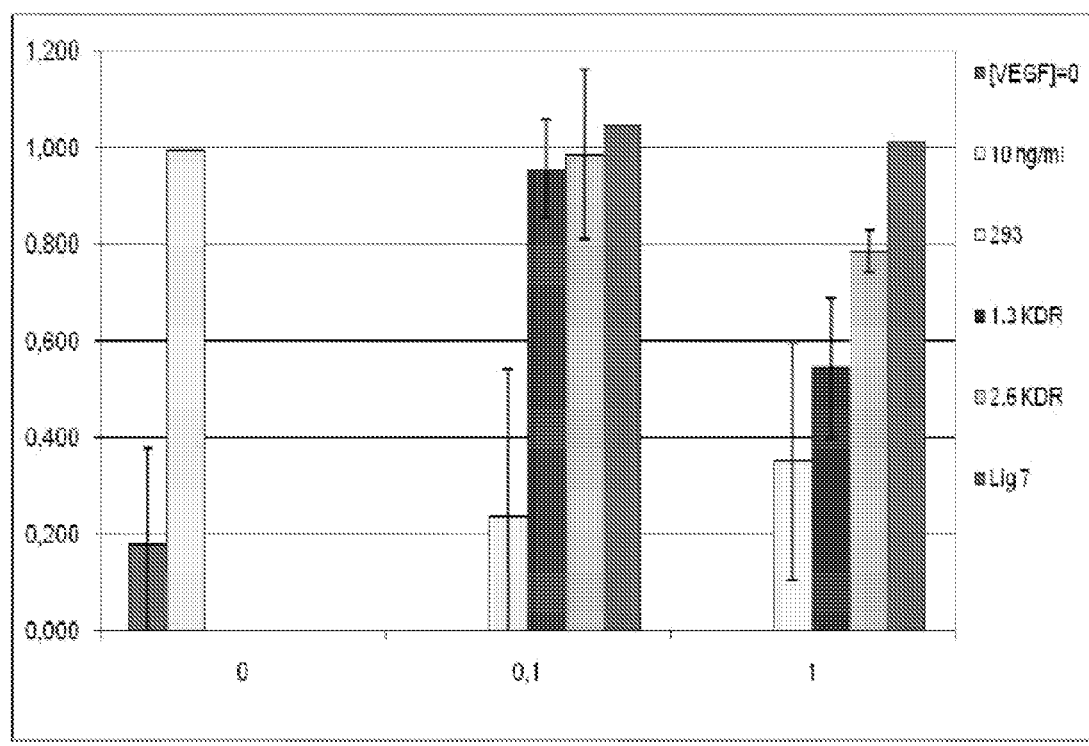
FIGURE 13: The effect of the recombinant antibodies on VEGF-HUVEC interactions by cell proliferation assay.

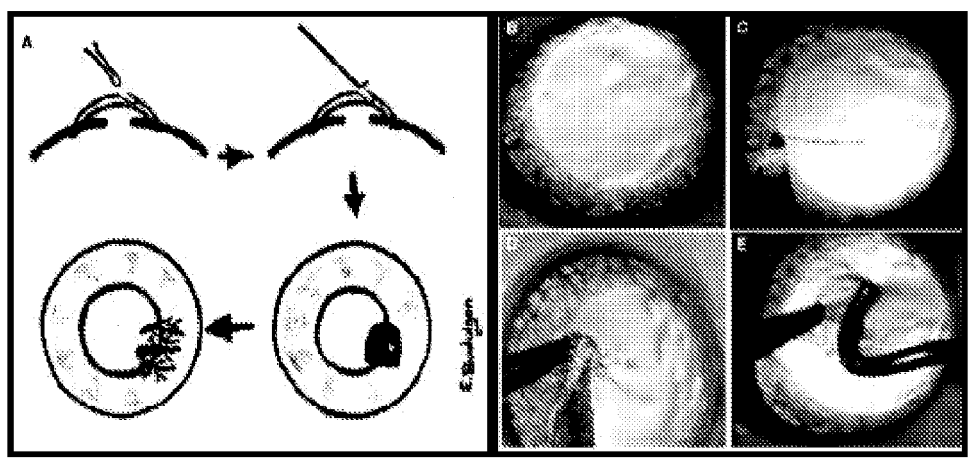
FIGURE 14: Schematic and photographic illustration of cornea angiogenesis application

FIGURE 17

TABLE 1

TABLE 1: Biopanning steps for the selection and enrichment of scFv able to bind to sKDR.

| Biopanning number | 1 | 2 | 3 |
|---|---|---|---|
| phage amount entered to biopanning (cfu/ml) | $2\times10^{11}$ | $2\times10^{11}$ | $10^{11}$ |
| Eluted phage amount after biopanning (cfu/ml) | $4\times10^{2}$ | $2\times10^{3}$ | $10^{2}$ |

The amount of phages entered to biopanning and eluted after biopanning is indicated as colony forming unit per ml (cfu).

SEQUENCE LISTING

```
<160> NUMBER OF SEQ ID NOS: 34

<210> SEQ ID NO 1
<211> LENGTH: 8
<212> TYPE: PRT
<213> ORGANISM: Mus musculus

<400> SEQUENCE: 1

Gly Asp Ser Ile Thr Ser Gly Asn
1               5

<210> SEQ ID NO 2
<211> LENGTH: 7
<212> TYPE: PRT
<213> ORGANISM: Mus musculus

<400> SEQUENCE: 2

Ile Ser Tyr Ser Gly Ser Thr
1               5

<210> SEQ ID NO 3
<211> LENGTH: 10
<212> TYPE: PRT
<213> ORGANISM: Mus musculus

<400> SEQUENCE: 3

Ala Arg Tyr Gly Gly Asn Tyr Phe Asp Tyr
1               5                   10

<210> SEQ ID NO 4
<211> LENGTH: 5
<212> TYPE: PRT
<213> ORGANISM: Mus musculus

<400> SEQUENCE: 4

Ser Ser Val Ser Tyr
1               5

<210> SEQ ID NO 5
<211> LENGTH: 3
<212> TYPE: PRT
<213> ORGANISM: Mus musculus

<400> SEQUENCE: 5

Asp Thr Ser
1

<210> SEQ ID NO 6
<211> LENGTH: 9
<212> TYPE: PRT
<213> ORGANISM: Mus musculus

<400> SEQUENCE: 6

Phe Gln Gly Ser Gly Tyr Pro Leu Thr
1               5
```

<210> SEQ ID NO 7
<211> LENGTH: 115
<212> TYPE: PRT
<213> ORGANISM: Mus musculus

<400> SEQUENCE: 7

Val Lys Leu Gln Gln Ser Gly Pro Ser Leu Val Lys Pro Ser Gln Thr
1               5                   10                  15

Leu Ser Leu Thr Cys Ser Val Thr Gly Asp Ser Ile Thr Ser Gly Asn
            20                  25                  30

Trp Asn Trp Ile Arg Lys Phe Pro Gly His Lys Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Phe Phe Leu Gln
65                  70                  75                  80

Leu Asn Ser Val Thr Thr Glu Asp Thr Ala Thr Tyr Tyr Cys Ala Arg
                85                  90                  95

Tyr Gly Gly Asn Tyr Phe Asp Tyr Trp Gly Gln Gly Thr Thr Val Thr
            100                 105                 110

Val Ser Ser
        115

<210> SEQ ID NO 8
<211> LENGTH: 108
<212> TYPE: PRT
<213> ORGANISM: Mus musculus

<400> SEQUENCE: 8

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Arg Thr Lys Leu Glu Leu Lys Arg Ala
            100                 105

<210> SEQ ID NO 9
<211> LENGTH: 24
<212> TYPE: DNA
<213> ORGANISM: Mus musculus

<400> SEQUENCE: 9
ggcgactcca tcaccagtgg taac                                          24

<210> SEQ ID NO 10
<211> LENGTH: 21
<212> TYPE: DNA
<213> ORGANISM: Mus musculus

<400> SEQUENCE: 10

```
ataagctaca gtggtagcac t                                              21

<210> SEQ ID NO 11
<211> LENGTH: 30
<212> TYPE: DNA
<213> ORGANISM: Mus musculus

<400> SEQUENCE: 11
gcaagatatg gtggtaacta ctttgactac                                     30

<210> SEQ ID NO 12
<211> LENGTH: 15
<212> TYPE: DNA
<213> ORGANISM: Mus musculus

<400> SEQUENCE: 12
tcaagtgtaa gttac                                                     15

<210> SEQ ID NO 13
<211> LENGTH: 9
<212> TYPE: DNA
<213> ORGANISM: Mus musculus

<400> SEQUENCE: 13 gacacatcc                                                             9

<210> SEQ ID NO 14
<211> LENGTH: 27
<212> TYPE: DNA
<213> ORGANISM: Mus musculus

<400> SEQUENCE: 14
tttcagggga gtgggtaccc actcacg                                        27

<210> SEQ ID NO 15
<211> LENGTH: 348
<212> TYPE: DNA
<213> ORGANISM: Mus musculus

<400> SEQUENCE: 15
caggtgaagc tgcagcagtc aggacctagc ctcgtgaaac cttctcagac tctgtccctc    60
acctgttctg tcactggcga ctccatcacc agtggtaact ggaactggat ccggaaattc   120
ccagggcata aacttgagta catggggtac ataagctaca gtggtagcac ttattataat   180
ccatctctca aaagtcgaat ctctatcact cgagacacat ccaagaacca gttcttcctg   240
cagttgaatt ctgtgactac tgaggacaca gccacatatt actgtgcaag atatggtggt   300
aactactttg actactgggg ccaagggacc acggtcaccg tctcctca               348

<210> SEQ ID NO 16
<211> LENGTH: 324
<212> TYPE: DNA
<213> ORGANISM: Mus musculus

<400> SEQUENCE: 16
gacatcgagc tcactcagtc tccagcaatc atgtctgcat ctccagggga gaaggtcacc    60
atgacctgca gtgccagctc aagtgtaagt tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgaa   240
```

```
gatgttgcca cttattactg ttttcagggg agtgggtacc cactcacgtt cggtgctagg    300
accaagctgg agctgaaacg ggcg                                           324
```

<210> SEQ ID NO 17
<211> LENGTH: 8
<212> TYPE: PRT
<213> ORGANISM: Mus musculus

<400> SEQUENCE: 17

Gly Tyr Ala Phe Ile Gly Tyr Asn
1               5

<210> SEQ ID NO 18
<211> LENGTH: 8
<212> TYPE: PRT
<213> ORGANISM: Mus musculus

<400> SEQUENCE: 18

Ile Asp Pro Tyr Tyr Cys Gly Thr
1               5

<210> SEQ ID NO 19
<211> LENGTH: 14
<212> TYPE: PRT
<213> ORGANISM: Mus musculus

<400> SEQUENCE: 19

Ala Arg Gly Thr Met Ile Thr Thr Ser Tyr Ala Met Asp Tyr
1               5                   10

<210> SEQ ID NO 20
<211> LENGTH: 5
<212> TYPE: PRT
<213> ORGANISM: Mus musculus

<400> SEQUENCE: 20

Ser Ser Val Ser Tyr
1               5

<210> SEQ ID NO 21
<211> LENGTH: 4
<212> TYPE: PRT
<213> ORGANISM: Mus musculus

<400> SEQUENCE: 21

Ala Thr Ser Asn
1

<210> SEQ ID NO 22
<211> LENGTH: 9
<212> TYPE: PRT
<213> ORGANISM: Mus musculus

<400> SEQUENCE: 22

Gln Gln Trp Ser Ser Asn Leu Leu Thr
1               5

<210> SEQ ID NO 23
<211> LENGTH: 121
<212> TYPE: PRT
<213> ORGANISM: Mus musculus

<400> SEQUENCE: 23

Gln Val Lys Leu Gln Glu Ser Gly Pro Glu Leu Lys Pro Gly Ala
1               5                   10                  15

Ser Val Lys Ile Ser Cys Lys Ala Ser Gly Tyr Ala Phe Ile Gly Tyr
            20                  25                  30

Asn Met Asn Trp Val Lys Lys Ser Asn Glu Lys Ser Leu Glu Trp Ile
        35                  40                  45

Gly Asn Ile Asp Pro Tyr Tyr Cys Gly Thr Ser Tyr Asn Gln Lys Phe
    50                  55                  60

Lys Gly Lys Ala Thr Met Thr Val Asp Glu Ser Ser Thr Ala Phe
65                  70                  75                  80

Met Gln Leu Lys Ser Leu Thr Ser Glu Asp Ser Ala Val Tyr Tyr Cys
                85                  90                  95

Ala Arg Gly Thr Met Ile Thr Thr Ser Tyr Ala Met Asp Tyr Trp Gly
                100                 105                 110

Gln Gly Thr Thr Val Thr Val Ser Ser
            115                 120

<210> SEQ ID NO 24
<211> LENGTH: 108
<212> TYPE: PRT
<213> ORGANISM: Mus musculus

<400> SEQUENCE: 24

Asp Ile Glu Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Ser Cys Gln Gln Trp Ser Ser Asn Leu Leu Thr
                85                  90                  95

Phe Gly Ala Gly Thr Lys Leu Glu Ile Lys Arg Ala
                100                 105

<210> SEQ ID NO 25
<211> LENGTH: 24
<212> TYPE: DNA
<213> ORGANISM: Mus musculus

<400> SEQUENCE: 25
ggttacgcat tcattggcta caac                                          24

<210> SEQ ID NO 26
<211> LENGTH: 24
<212> TYPE: DNA
<213> ORGANISM: Mus musculus

<400> SEQUENCE: 26
attgatcctt actattgtgg gact                                          24

<210> SEQ ID NO 27
<211> LENGTH: 42
<212> TYPE: DNA
<213> ORGANISM: Mus musculus

<400> SEQUENCE: 27
gcaaggggga ctatgattac gacgtcctat gctatggact ac         42

<210> SEQ ID NO 28
<211> LENGTH: 15
<212> TYPE: DNA
<213> ORGANISM: Mus musculus

<400> SEQUENCE: 28
tcaagtgtaa gttac                                        15

<210> SEQ ID NO 29
<211> LENGTH: 12
<212> TYPE: DNA
<213> ORGANISM: Mus musculus

<400> SEQUENCE: 29
gccacatcca ac                                           12

<210> SEQ ID NO 30
<211> LENGTH: 27
<212> TYPE: DNA
<213> ORGANISM: Mus musculus

<400> SEQUENCE: 30
cagcagtgga gtagtaacct gctcacg                           27

<210> SEQ ID NO 31
<211> LENGTH: 363
<212> TYPE: DNA
<213> ORGANISM: Mus musculus

<400> SEQUENCE: 31
caggtcaaac tgcaggagtc tggacctgag ctggagaagc ctggcgcttc agtgaagatt    60
tcctgcaagg cttccggtta cgcattcatt ggctacaaca tgaactgggt gaagaagagc   120
aatgaaaaga gccttgagtg gattggaaat attgatcctt actattgtgg gactagctac   180
aaccagaagt tcaagggcaa ggccacaatg actgtagacg aatcctccag cacagccttc   240
atgcagctca agagcctgac atctgaggac tctgcagtct attactgtgc aaggggggact   300 atgattacga cgtcctatgc tatggactac tggggccaag ggaccacggt caccgtctcc   360
tca                                                                 363

<210> SEQ ID NO 32
<211> LENGTH: 324
<212> TYPE: DNA
<213> ORGANISM: Mus musculus

<400> SEQUENCE: 32
gacatcgagc tcactcagtc tccagcaatc ctgtctgcgt ctccagggga gaaggtcaca    60
atgacttgca gggccagctc aagtgtaagt tacatgcact ggtaccagca gaagccagga   120
tcctccccca aaccctggat ttatgccaca tccaacctgg cttctggagt ccctgctcgc   180
ttcagtggca gtgggtctgg gacctcttac tctctcacaa tcagcagagt ggaggctgaa   240
gatgctgcca cttattcctg ccagcagtgg agtagtaacc tgctcacgtt cggtgctggg   300
accaagctgg aaataaaacg ggcg                                         324

<210> SEQ ID NO 33
<211> LENGTH: 14

```
<212> TYPE: PRT
<213> ORGANISM: Artificial Sequence
<220> FEATURE:
<223> OTHER INFORMATION: synthetic peptide linker

<400> SEQUENCE: 33

Gly Gly Gly Ser Gly Gly Gly Gly Ser Gly Gly Gly Gly Ser
1               5                   10

<210> SEQ ID NO 34
<211> LENGTH: 42
<212> TYPE: DNA
<213> ORGANISM: Artificial Sequence
<220> FEATURE:
<223> OTHER INFORMATION: synthetic linker

<400> SEQUENCE: 34
ggaggcggtt caggcggagg tggctctggt ggtggcggat cg                         42
```

RECOMBINANT ANTIBODY STRUCTURES BINDING TO AND BLOCKING THE ACTIVITY OF VASCULAR ENDOTHELIAL GROWTH FACTOR 2 (VEGFR—2/KDR)

TECHNICAL FIELD OF THE INVENTION

The primary object of the present invention is to obtain recombinant single-chain variable fragment antibodies that could be involved as an inhibitor in angiogenesis, which plays a pivotal role in tumor development, and thus in disease mechanisms related to angiogenesis, via interacting with VEGFR2 (extracellular domain).

BACKGROUND OF THE INVENTION

Oxygen and nutrients required for the development of living tissues are carried to the tissues through the blood vessels whereas waste substances are carried away from the tissues via the blood vessels as well. While angiogenesis, growth of new blood vessels from pre-existing vessels, is a physiological phenomenon in embryogenesis, wound healing, and during menstruation in the female reproductive system, it emerges pathologically in inflammatory diseases such as arthritis, chronic inflammation, inflammatory bowel diseases, and psoriasis and such cancers of various tissues as breast, bladder, colon, lung, neuroblastoma, melanoma, kidney, pancreas, uterus, cervix, and glioblastoma as well as in ophthalmologic diseases such as age related macular degeneration.

The significance of angiogenesis in in vivo formation, development, and metastasis of solid tumors was first asserted in 1971 (Folkman J., 1971, *N Eng J Med.*, 285, 1182-1186). Angiogenesis emerges through the proliferation of capillary endothelial cells (Risau W, 1997, *Nature*, 386, 671-674). As with all biological events, the organism responds to angiogenic stimulation by secreting antiangiogenic factors. Proangiogenic factors and antiangiogenic factors are at equilibrium under normal conditions and when this equilibrium is disturbed against antiangiogenic factors, angiogenesis starts. Vascular Endothelial Growth Factor (VEGF) was defined by Ferrara et al. in 1989 (Ferrara and Henzel, 1989 *Biochem Biophys Res Commun* 161, 851-858). VEGF plays a key role in angiogenesis (Ferrara N et al., 1996, *Nature*, 380: 439-442). Experiments on mice showed that the only lack of allele concerning VEGF resulted in early embryonic lethality due to serious vascular problems (Carmilet P. et al., 1996, *Nature*, 380, 435-439). VEGF is a heparin-binding homodimeric basic protein bound with disulfide bond of 45 kDa in weight. Such various sub-groups of it as VEGF-A, VEGF-B, VEGF-C, VEGF-D ve VEGF-E have been defined so far. In mammals, VEGF-A has isoforms such as $VEGF_{121}$, $VEGF_{165}$, $VEGF_{189}$, $VEGF_{206}$ and $VEGF_{145}$ based on the number of amino acids. Among these isoforms, $VEGF_{165}$ is the predominant one (Ferrara N., et al., 2009, *Arterioscler. Thromb. Vasc. Biol.*, 29, 789-791,).

VEGF shows its intracellular effects by binding to tyrosine kinase receptors in cell membranes. VEGF Receptors contain two portions. The first section is the intracellular portion containing a tyrosine-kinase domain. The second portion is the extracellular region comprising 5 to 7 immunoglobulin-like structures that contain ligand binding regions (Ferrara N. et al., 2003, *Nat. Med.* 9:669-676). In addition to identification of Flt-1 (VEGFR-1), flk-1/KDR (VEGFR-2), and Flt-4 (VEGFR-3) as VEGF receptors, receptor structures termed neuropilin-1 and neuropilin-2 expressed at the endothelial cell surface and that has a low binding characteristic to VEGF-A have been defined recently. KDR (kinase-insert-domain-containing receptor) was defined by Terman et al. by patent numbered PCT/US92/01300 in 1991 (Terman et al., 1991, *Oncogene* 6:1677-1683). Flk-1 sequence was shed light upon by sequencing method in 1991 (Mathhews W et al., 1991, *Proc. Natl. Acad. Sci. U.S.A*, 88:9026-9030). These studies have demonstrated that KDR is the human analog of FLK-1 receptor. In addition, KDR and FLK-1 receptors are also known as VEGFR2.

The most important of VEGF receptors is KDR (VEGFR-2), which is responsible for endothelial cell proliferation and chemotaxis (Ferrara N et al., 2003, *Nat Med.*, 9, 669-676). VEGFR-2 (Kinase insert domain receptor/KDR) is expressed at high levels in vascular endothelial cells and hematopoietic cells (Asahara T., et al., 1997, *Science*, 275, 964-967; Ziegler B l. et al., 1999, *Science*, 285, 1553-1558; Peichev M., et al., 2000, *Blood*, 95, 952-958). The 7 immunoglobulin like domains present in the extracellular section of KDR enable the signals from the environment to be transducted to the cytoplasm of the cell. The intracellular section of KDR mediates intracytoplasmic signal transduction. Therefor, any molecule aiming to inhibit the interacion VEGF with KDR should target the 1-7 immunoglobulin-like extracellular domains of the receptor (LU D. ve ark., 2000, *JBC*, 275, 14321-14330).

Several studies conducted so far have found that VEGF increases in many types of cancers such as glioblastoma, colorectal cancer, non-small cell lung, pancreas, ovary, acute myeloid leukemia, multiple myeloma, Hodgkin's disease and non-Hodgkin's, and myeloma (Ranieri G et al., 2006, *Curr Med Chem.*, 13, 1845-1857). Therefore, VEGF and VEGF receptors are among the priority targets in suppression of angiogenesis. It is possible to prevent function of VEGF by inhibiting from different angles the signal path triggered by binding of VEGF to transmembrane tyrosine kinase receptors on endothelial cells with structures developed against VEGF and VEGF receptors.

Although the binding affinity of VEGF to VEGFR-1 (Flt-1) is 50 times more as compared with VEGFR-2 (KDR), VEGF's angiogenic features, endothelial cell proliferation and its effect on chemotaxis, take place due to its relation with KDR (Cross M. et al., 2003, *Trends in Biochemical Sciences;* 28.488-494). It has been demonstrated that when a plasmid encoding VEGFR2 is given to pig aortic endothelial cells lacking VEGFR2, these cells go through mitosis and participate in chemotaxis (Shibuya M et al., 1990, *Oncogene*, 8:519-524). Some studies on mice showed that these animals lacked organized blood vessels in deficient or defective expression of VEGFR2. Shalaby et al. showed that mouse embryos lacking VEGFR-2 expression die during the early embryonic period due to the deficiency in the development of endothelial and hematopoietic progenitor cells (Shalaby F et al., 1995, *Nature.* 376 (6535):62-6). With this experiment, it has been shown that blocking the relation between VEGF and KDR is important in terms of suppression of angiogenesis.

In 1971, J. Folkman asserted that growth of a tumor is dependent on oxygen and energy resources carried by new capillaries that develop from the blood vessels located near the tumor and claimed that antiangiogenic attempts may be an effective approach in terms of preventing cancer development. The close association of tumor growth with angiogenic activity has led to investigation of angiogenic agents as additional options of treatment in cancer treatment. Demonstration of the fact that antibodies developed against VEGF suppress tumor growth in vivo (Kim K J et al., 1993, *Nature* 362: 841-844) has shown that VEGF antagonists may be used in treatment as inhibitors of tumor vascularization. Today, VEGF and VEGF receptors are among the priority objectives in the suppression of angiogenesis and thereby, in oncology (Ferrara N and Kerbel R. S., 2005, *Nature.* 438: 967-974)

Several anti-angiogenic strategies based on blocking VEGF/receptor relationship have been developed in recent years. Within this framework, such various structures as anti-VEGF antibodies that prevent VEGF/KDR interaction and/or suppress KDR signal transmission for the inhibition of angiogenesis and tumor (Kanai et al., 1998, J. Cancer 77, 933-936; Margolin et al., 2001, J. Clin. Oncol. 19, 851-856); anti-KDR antibodies (Zhu et al., 1998, Cancer Res. 58, 3209-3214; Zhu et al., 2003, Leukemia 17, 604-61 1; Prewett et al., 1999, Cancer Res. 59, 5209-5218); anti-VEGF immunotoxins (Olson et al. 1997, Int. J. Cancer 73, 865-870); ribozymes (Pavco et al., 2000, Clin. Cancer Res. 6, 2094-2103); soluble receptors (Holash et al., 2002, Proc. Natl. Acad. Sci. USA 99, 11393-11398); tyrosine kinase inhibitors (Fong et al., 1999, Cancer Res 59, 99-106; Wood et al., 2000, Cancer Res 60, 2178-2189; Grosios et al., 2004, Inflamm Res. 53(4):133-42); anti-VEGF-antisense (Forster et al. 2004, Cancer Lett. 20; 212(1):95-103); and RNA interference (Takei et al. 2004, Cancer Res. 64 (10):3365-70; Reich et al., 2003, Mol Vis 9:210-6).

Studies focusing on suppression of angiogenesis by targeting VEGF and receptors have intensified. Many strategies have been developed to this end. The rhuMab VEGF (Bevacizumab), recombinant human monoclonal VEGF antibody with antiangiogenic and anti-tumor activity (Monk B. J. et al., 2005, *Gynecologic Oncology,* 96, 902-905) and the monoclonal human antibody developed in 2006 by Wu Y et al. (Wu Y, et al., 2006 *Clin. Cancer Res.,* 12(21), 6573-84) against VEGFR-1'e are the most important ones. Results indicating that VEGF-Trap glioma-animal models with VEGFR1 and VEGFR2 hybrid structures combined to human IgG1 constant region can be used in treatment of tumors in the beginning and advanced stages (Gomez-Manzano C. et al., 2008, *Neuro-Oncology,* 10, 940). Ranibizumab, 48 kDa, comprised of the Fab (antigen-binding) section of Anti-VEGF monoclonal antibody, renders lighter and thinner than the monoclonal antibody Bevacuzumab (148 kDa) it is derived from, and thereby, is able to pass through the internal membrane in intravitreal application and inhibits all VEGF isoforms (Gaudreault J. et al., 1999, *Am Assoc Pharm Sci Pharm Sci Suppl,* 1, 2142). Today, promising results have been obtained in the use of Ranibizumab for treatment in age related macular degeneration (Rosenfeld P. J., et al., 2006, *N Engl J Med.,* 355, 1419-1431).

In addition to monoclonal antibody structures, the use of small molecules as VEGF antagonists through acting as VEGF receptor tyrosine kinase inhibitors is possible as well. In a study conducted by Bainbridge J. W. B. et al. in 2003 with peptide structures created by setting off from the exon 6 region, where interaction of the VEGF molecule with KDR take place, 7 amino acid structures that inhibit angiogenesis by blocking interaction of VEGF with its receptor were identified in vitro. Recently, sunitinib and sorafenib, two small molecule VEGF receptor tyrosine kinase inhibitors, have been started to be used in cancer treatments (KO J. S et al., 2009, *Clin. Cancer Res.,* 15(6), 2148-2157; Jilaveanu L. et al., 2009, *Clinical Cancer Research,* 15, 1076).

In line with the developments in genetic engineering in recent years, formation of functional recombinant antibody fragments that mimic antigen recognition of the antibody molecule has been possible. Expressed as an antibody fragment, single chain variable fragment is constituted by binding of heavy chain variable region ($V_H$) and light chain variable region ($V_L$) via a peptide bridge. These antibody fragments are called single chain variable fragments (scFv) (U.S. Pat. No. 4,946,778 Lander et al.; WO88/09344, Huston et al.). As ScFv structures contain antigen-binding variable regions (Fv), they have the characteristic to provide the binding feature of the antibody molecule at a minimal structure. On the other hand, single domain antibody structures may be effective in binding to the target antigen structure.

In 1993, Jeffrey et al. showed that heavy chain was fundamental in digoxin binding of the antibody developed against digoxin (Jeffrey, P. D. et al. Proc. Nat. Acad. Sci., USA 1993, 90:10310-103149). It has been shown in a recent study that the "nanobody" structures consisting of heavy chain variable fragments of the antibody developed against the epidermal growth factor receptor (EGFR) prevents binding of Epidermal growth factor (EGF) to EGFR (Roovers R. et al., 2007, *Cancer Immunology* 15:303-317). ScFv's are presented on the surfaces of filamentous phages in phage display technology (WO 92/01047 Mc Cafferty et al.). It is possible to develop nanoantibody structures against VEGFR with this approach. However, rapid removal from circulation of nano antibody structures of approximately 15 kD leads to reservations in treatment applications. However, these nano antibody structures have been enabled to stay in the circulation for longer periods by restructuring them as 50 kD multivalent to ensure that they are provided with the feature to bind to albumin (Tijink B et al. 2008, Mol Cancer Therapy. 7(8): 2288-2297).

The use of filamentous phages in phage display technology has brought about various advantages. Easy purification of phage particles from culture supernatant, accessibility to genetic and sequence data, and the opportunity to select the small number of phage clones that can identify the target antigen from among many antigens using the "biopanning" method are some of these advantages. Phagemid vectors that contain both bacteriophage replication origin and plasmid replication origin are preferred in order to take advantage of this convenience in phage display technology. The multiple cloning site (MCS) in these phagemid vectors is located at the start point of the gene that belongs to the sheath structural protein of the phagemid (e.g., gIII) Thus, the product obtained as a result of fusions made on sheath proteins can mimic the antibody located on the surface of B-lymphocytes existing in the immune system in the normal environment. However, this process is dependent upon how the amber stop codon located between the antibody gene and gIII will be read by the host bacteria. If phage supE grows on a suppressive host (e.g., *E. coli* TG1), the antibody fragment makes fusion to the minor sheath protein and stays on the phage surface. This structure on phage surface can act as a receptor that detects such foreign structures as B surface antibodies. If phage is grown on non-suppressive (sup⁻) *E. coli* strains (such as HB2151), then amber codon will be read as stop codon and the antibody particle will be secreted from the bacteria in soluble form. As such, mimicking of the antibodies synthesized from plasma cells with phagemid vectors become possible. The region comprised of 6 histidines on the phagemid vector, following the expression of cloned gene fragment to the multiple cloning site as dissolved in non-suppressor bacteria, enables easy purification of this recombinant protein from the environment using $Zn^{++}$, $Ni^{++}$ or $Co^{++}$ charged affinity column (Weiner L. M, 1996, *J. Mol. Biol.,* 255(1), 28-43).

Due to the technical convenience of the phage display technology, the scFv structure reflects a wide range of utilization opportunities in many disciplines. In contrast to the approximately 150 kDa size of the whole antibody molecule, the scFv structures of the antibody, which are approximately 30 kDa in size and lack the constant region and Fc parts of the antibody, are being used in today's medical researches focusing on diagnosis and treatment in increasing numbers (Bradbury A. R. M. et al., 2004, *Journal of Immunological Methods,* 290, 29-49).

The KDR 1.3 and 2.6 scFv antibody structures mentioned in the invention present antiangiogenic characteristics by blocking the intracellular signaling activity of VEGFR-2 by binding to the extracellular part of the VEGFR2 (1-7 immunoglobulin domain) on the cell surface and by inhibiting VEGF dependent cell proliferation.

TECHNICAL PROBLEMS INTENDED TO BE SOLVED BY THE INVENTION

In 1971, J. Folkman stated that growth of a tumor is dependent on oxygen and energy resources carried by new capillaries that develop from the blood vessels located near the tumor and asserted that attempts to block angiogenesis may be an effective approach in terms of preventing cancer development (Folkman J., 1971 *N Eng J Med.,* 285, 1182-6). Various studies have proved that antiangiogenic approaches are promising in cancer treatment (Kim K J et al., 1993 *Nature* 362: 841-844). The close association of cancer development, the most significant pathological phenomenon due to the high rate of mortality, with angiogenic activity has particularly led the way to investigation of antiangiogenic agents as a new option in cancer therapy.

In recent years, VEGF and VEGF receptors that play a key role in angiogenesis have been focused on as a target in the development of antiangiogenic structures). The first sign to show that structures developed against VEGF may be useful in cancer treatment was obtained from a mouse neuroblastoma model created using a neutralizing antibody (Mordenti J, 1999 *Toxicol Pathol.* 27(1):14-21). This study demonstrated that anti-VEGF neutralizing antibody structure blocks tumor growth. The results of this study have encouraged studies aimed at developing structures blocking VEGF and its receptors to prevent tumor growth. These studies have made it possible to obtain new structures that can be used in anticancer treatment activities such as anti-HIF (anti-Hypoxia-Inducible Factor) agents, VEGF antisense oligonucleotides, VEGF ribosomes, soluble VEGF receptors, anti-VEGF receptor antibodies, and VEGF DNA vaccines (Ferrara N., et al.., 2003, *Nat Med.,* 9, 669-676).

Antibodies developed against VEGF have been found to slow tumor growth (Hicklin et al., 2001, *DTT* 6: 517-528). Although mouse monoclonal antibodies are widely employed in clinical laboratory diagnosis, their success is limited in treatment applications in humans. The primary reason of this is activation of the immune response that develop against mouse antibodies following repeated doses in approximately 80% of patients treated with mouse antibodies. In addition, Fc part of mouse antibodies plays a less effective role in the human immune system and mouse antibodies have a shorter half-life as compared with human antibodies in treatment applications. These reasons limit the use of mouse antibodies in treatment applications.

Genetech Inc. launched recombinant humanized anti-VEGF monoclonal antibody structure in 2000 (bevacizumab; U.S. Pat. No. 6,054,297). This antibody structure is used in treatment of colon cancers today and it is being tested on other types of tumor cells. It is estimated that treatments based on bevacizumab bring about an additional treatment cost of USD 42.800 to 55.000 per patient and consequently, an extra expenditure of USD 1.5 billion will be made for advanced colon cancer treatments only in the United States. Therefore, there is a need for the development of new anti-angiogenic structures as alternatives such as recombinant antibodies, which cost less to produce in high volumes in bacteria and thereby, will reduce treatment costs.

Various studies conducted so far have demonstrated that phage display technology can be an effective method in the identification of new recombinant antibody structures that can prevent angiogenesis. Antibody structures in single-chain variable fragment form have been obtained following immunization of Balb/c mice with extracellular domain of KDR (KDR-AP) produced through human placental alkaline phosphatase fusion (WO 00/44777, Zhu Z, 2000). Employing the phage display technology and using human antibody libraries, antibody structures that are candidates for antiangiogenic applications against KDR in the form of Fab and chimeric antibody have been developed (PCT/US03/06459, Zhu Z, 2003).

Unlike the studies developed targeting antiangiogenic applications outlined above, in the patent study presented herewith, instead of the antibodies that are approximately 150 kDa in size, phage display method has been employed to obtain recombinant single-chain variable fragment antibodies 33 kDa in size following the selection against KDR (1-7) from the recombinant antibody library developed after immunization induced in BALB/c J mice with recombinant KDR (1-7). The antigen used in the development of these antibody structures and the sequence of complementarity determining regions (CDR) of the recombinant antibody obtained after the selection are different from those in the studies as well as patents mentioned above.

DESCRIPTION OF THE FIGURES

FIG. 1: Agarose gel electrophoresis image of variable light and heavy chains of the scFv produced against KDR. 1—pUC19/Hinf I digestion; 2—$V_H$ PCR product; 3—$V_L$ PCR product FIG. 2: Agarose gel electrophoresis image of single chain variable fragment produced from the ligation of variable light and heavy chains with a linker coding for $(Gly_4Ser)_3$. 1—ScFv marker (750 bp); 2—ScFv library; 3—ScFv library FIG. 3: Colony PCR results of randomly selected colonies obtained from the transformation *E. coli* TG1 bacteria with the ligation product of KDR1.3 scFv. 1—pUC19/Hinf I digestion; 2—ScFv marker (750 bp); 3—PCR of control ScFv; 4—Negative control of PCR; 5—empty; 6—Colony PCR; 7—Colony PCR; 8—Colony PCR; 9—Colony PCR; 10—empty; 11—Colony PCR; 12—Colony PCR; 13—Colony PCR; 14—Colony PCR (KDR 1.3 scFv present).

FIG. 4: Colony PCR results of randomly selected colonies obtained from the transformation *E. coli* TG1 bacteria with the ligation product of KDR2.6 scFv. 1—pUC19/Hinf I digestion; 2—ScFv marker (750 bp); 3—Negative control of PCR; 4—PCR of control ScFv; 5—empty; 6—Colony PCR; 7—Colony PCR; 8—Colony PCR; 9—Colony PCR; 10—empty; 11—Colony PCR (KDR2.6 scFv present); 12—Colony PCR; 13—Colony PCR; 14—Colony PCR (KDR 1.3 scFv present).

FIG. 5: BstnI digestion profile of KDR1.3 and KDR2.6 scFv clones. 1—Marker; 2—KDR1.3 scFv; 3—Bstn I digestion of KDR1.3 scFv; 4—Bstn I digestion of KDR2.6 scFv; 5—KDR2.6 scFv.

FIG. 6: DNA sequence of KDR1.3 scFv and the emplacement of CDR regions predicted from IMGT web site.

FIG. 7: DNA sequence of KDR2.6 scFv and the emplacement of CDR regions predicted from IMGT web site.

FIG. 8: SDS-PAGE and western blot analysis results of the KDR 1.3 recombinant antibody. A; Coomassie staining of SDS-PAGE gel of purified KDR 1.3 scFv. B; Western Blot analysis of purified KDR 1.3 scFv. The loading order and amount was the same for both gels. 1—Marker (Fermentas SM0441); 2—Pellet after 4 hours of induction, $T_4$; 3—The supernatant after the first step of purification; 4—The supernatant after the second step of purification; 5—The supernatant after the third step of purification; 6—The supernatant after the fourth step of purification; 7—The supernatant after the fifth step of purification; 8—The supernatant after the sixth step of purification; 9—The pellet after the sixth extraction step; 10—Control ScFv (Lig 7).

FIG. 9: SDS-PAGE and western blot analysis results of the KDR 2.6 recombinant antibody. A; Coomassie staining of SDS-PAGE gel of purified KDR 2.6 scFv. B; Western Blot analysis of purified KDR 2.6 scFv. The loading order and amount was the same for both gels. 1—Marker (Fermentas SM0441); 2—Pellet after 4 hours of induction, $T_4$; 3—The supernatant after the first step of purification; 4—The supernatant after the second step of purification; 5—The supernatant after the third step of purification; 6—The supernatant after the fourth step of purification; 7—The supernatant after the fifth step of purification; 8—The supernatant after the sixth step of purification; 9—The pellet after the sixth extraction step; 10—Control ScFv (FIG. 7).

FIG. 10: SDS-PAGE and western blot analysis results of TALON affinity column purified KDR 1.3 scFv. A; Coomassie staining of SDS-PAGE gel of talon affinity column purified KDR 1.3 scFv. B; Western Blot analysis of talon affinity column purified KDR 1.3 scFv. The loading order and amount was the same for both gels 1—Marker (Fermentas SM0441); 2—The dialyzed supernatant after the sixth step of purification; 3—The first talon affinity column elution tube; 4—The second talon affinity column elution tube; 5—The third talon affinity column elution tube; 6—The fourth talon affinity column elution tube; 7—The fifth talon affinity column elution tube; 8—The sixth talon affinity column elution tube; 9—The seventh talon affinity column elution tube; 10—control ScFV (Lig7)

FIG. 11: SDS-PAGE and western blot analysis results of TALON affinity column purified KDR 2.6 scFv. A; Coomassie staining of SDS-PAGE gel of talon affinity column purified KDR 2.6 scFv. B; Western Blot analysis of talon affinity column purified KDR 2.6 scFv. The loading order and amount was the same for both gels 1—Marker (Fermentas SM0441); 2—The dialyzed supernatant after the sixth step of purification; 3—The first talon affinity column elution tube; 4—The second talon affinity column elution tube; 5—The third talon affinity column elution tube; 6—The fourth talon affinity column elution tube; 7—The fifth talon affinity column elution tube; 8—The sixth talon affinity column elution tube; 9—The seventh talon affinity column elution tube; 10—control ScFV (Lig7)

FIG. 12: ELISA results of TALON purified KDR 1.3, 2.6 and Lig7 (control) scFv. A; Wells coated overnight with antigen are displayed with black arrows. The antibodies added after antigen coating are displayed with red arrows. B; The ELISA OD405 values for the wells mentioned in A.

FIG. 13: The effect of the recombinant antibodies on VEGF-HUVEC interactions by cell proliferation assay. HUVE cells from passage 5 were cultivated in medium containing % 2 of FBS and various antibodies such as Ab 293, KDR 1.3, 2.6 and Lig7 as negative control scFv at two different concentrations (0.1 and 1 μg/ml).

FIG. 14: Schematic and photographic illustration of cornea angiogenesis application (Konya D. et al, *Neurosurgery*, 2005, Volume 56, No: 6, June p: 1339-1346).

FIG. 17: Table 1: Biopanning steps for the selection and enrichment of scFv able to bind to sKDR1-7.

DETAILED DESCRIPTION OF THE INVENTION

Figure 15:
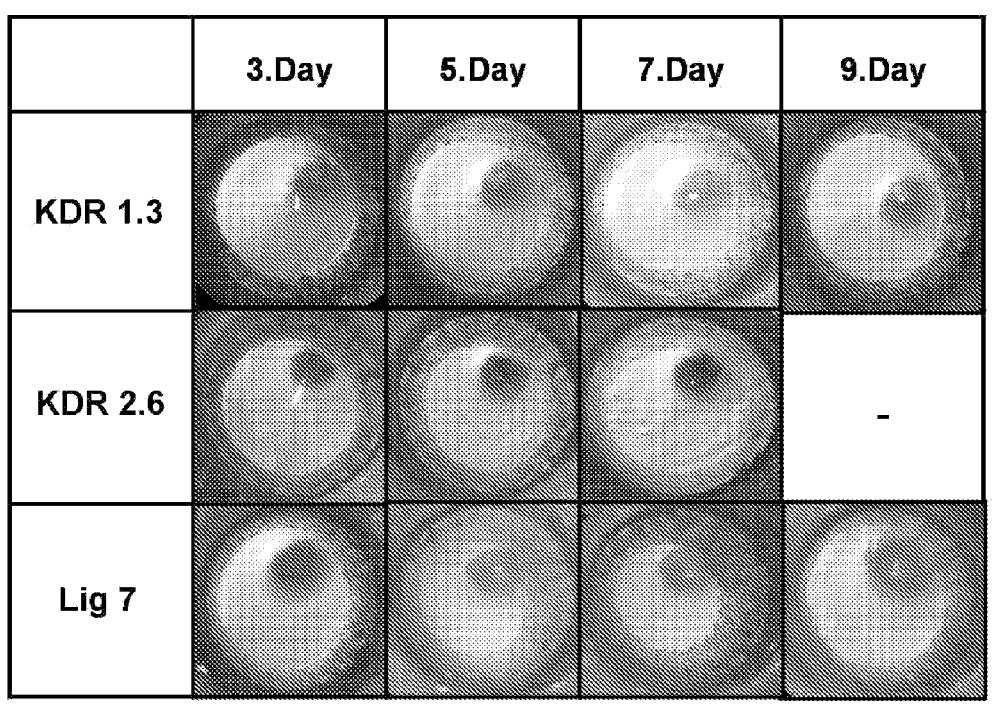
FIG. 15: Anti-angiogenic effectiveness of antibodies on the cornea angiogenesis model. Rat cornea fotographs of the experiment on angiogenesis inhibitory effect of the recombinant antibodies on arteriovenus malformation tissue grafted in rat cornea at day 3, 5, 7 and 9.

The invention presents recombinant antibody structures with antiangiogenic characteristics by blocking the intracellular signaling activity of VEGFR-2 by binding to the extracellular part of the VEGFR2 (1-7 immunoglobulin domain) on the cell surface and by inhibiting VEGF dependent cell proliferation.

Angiogenesis has been blocked with antibodies. The anti-VEGF antibody in market which is developed against anti-angiogenic practice, can not get into the retina and can hardly pass through vascular endothel because of its 148 kDa molecular weight. However, small recombinant antibody structures with low molecular weight do not have those disadvantages. It has been shown by the studies above that phage display technology may be an effective method in defining new antibody fragments that inhibit angiogenesis. However, the anti-angiogenic antibody fragments isolated up to today are such as human anti VEGF recombinant antibodies (Zhihua et al Appl Biochem Biotechnol (2008) 144:15-26), anti-VEGFR2 Fab fragments which was scanned against VEGFR2-Fc fusion protein, bisipesific antibodies (Shen et al: the journal of biological chemistry vol (2006). 281, 16: 10706-10714) or single chain Mouse antibodies obtained with KDR-AP immunization (Zhu et al, 1998, *Cancer Res*. 58, 3209-3214). VEGF's angiogenic features, endothelial cell proliferation and its effect on chemotaxis, take place due to its relation with extrcellular 1-7 domains of KDR. In the present invention, soluble extracellular 1-7 domains of VEGFR2 has been used for immunization and in screening of phage displayed antibody library. Thus, discovering recombinant antibodies that block the activity of VEGF, determining the nucleotide sequence that code this antibody structures, definition of new phages that code these sequences, development of new methods for the inhibition of angiogenesis of antibody structures that suppress the endothelial cell proliferation via cassation of the interaction between VEGF and its receptor, are the objectives of the presented discovery.

The term "recombinant antibody" refers to whole antibodies and any antigen-binding fragment (i.e., "antigen-binding portion," "antigen-binding polypeptide," or "immuno-binder") or single chain thereof.

The term "antigen-binding" refers to the ability to specifically bind to an antigen. It has been shown that the antigen-binding function of an antibody can be performed by fragments of a full-length antibody. a Fv fragment consisting of the VL and VH domains of a single arm of an antibody, (v) a single domain or dAb fragment (Ward et al., (1989) Nature 341:544-546), which consists of a VH domain; and (vi) an isolated complementarity determining region (CDR) or (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). These antibody fragments are obtained using conventional techniques known to those with skill in the art, and the fragments are screened for utility in the same manner as are intact antibodies.

[The term antibody as used in the scope of the present invention refers to an scFv antibody or an antibody fragment that binds a selected antigen. Thus, the scFv antibody of the present invention can be a full scFv comprising a VL and a VH domain which are linked by a short linker peptide comprising a linker of the sequence GGGSGGGGSGGGGSSGGGS (SEQ ID No: 33), The linkage of VL and VH can be in either orientation, VL-linker-VH or VH-linker-VL. In the presented invention, scFv structure is in VH-linker-VL orientation.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen The polypeptides of the invention may comprise conservative amino acid substitutions at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired target.

In a further aspect of the present invention KDR1.3 and KDR2.6 scFvs has 79% alignment score. The light chain variable domains (VL) of the two scFv mentioned in the present invention shows 90% alignment score and the heavy chain variable domains shows 60% alignment.

Complementary determining region (CDR) sequences was compared between KDR1.3 and KDR2.6 scFvs and the CDR regions of the scfv patented by Zhu et al. in 2000 (WO 00/44777). Full alignment was found between KDR1.3 and KDR2.6 (SEQ No:4 and SEQ No:20) for the CDRL1 region and it was found that a part of the CDRL1 region of Zhu's scFv was comprising the same sequence as SEQ No: 4 and SEQ No: 20. The CDRL2 region of Zhu's scFv has 75% alignment score with KDR2.6 CDRL2 region (SEQ No:21) and 66% alignment with KDR1.3 CDRL2 region (SEQ No:5). The alignment score of KDR1.3 and KDR2.6 scFvs for the CDRL2 region was 66%. The CDRL3 region of KDR1.3 and KDR2.6 were aligned with the CDRL3 region Zhu's scFv at a score of 55% but the alignment score for the same region between KDR1.3 and KDR2.6 was only 22%. The three CDRL3 region have all 9 amino acid and have a conscensus sequence (-Q-S----T), this might signify that the glutamine, the serine and the threonine amino acids are important for the interaction of the scFv's to KDR. Only one similarity of 50% was found between the CDRH3 region of KDR1.3 and Zhu's scFv. These results shows a high sequence conservation of the light chain variable region and its CDR regions compared to the heavy chain variable region for the recognition of the KDR molecule.

The invention encompasses any one of the VL sequences disclosed in combination with any one of the VH sequences disclosed so long as target binding specificity is maintained. The phages that bind to VEGFR-2 was primarily tested via ELISA method in order to examine their pre-findings concerning their blocking properties of the interaction between VEGF and human umbilical cord endothelial cells that express VEGF receptor on their surface (HUVEC). As a result of ELISA, KDR 1.3 and KDR 1.6 were defined. their effects on cell proliferation were examined and both of those recombinant were shown to have adverse effects on cell proliferation.

In an aspect of the present invention recombinant antibodies (KDR1.3 and KDR2.6) were provided that specifically binds VEGFR-2 and inhibits VEGF-induced proliferation of endothelial cells in vitro and angiogenesis in vivo Their anti-angiogenic effects on rat cornea in vivo model was demonstrated. This assay has the advantage that new blood vessels are easily detected and essentially must be newly formed blood vessels in the normally a vascular cornea. Statistical evaluations revealed that the anti-angiogenic activities of KDR 1.3 and KDR 2.6 antibodies were statistically significant (KDR 1.3; $p<0.05$ and KDR 2.6; $p<0.05$). But rat deaths occurred when KDR 2.6 antibodies was used. The in vivo experiments showed that KDR 1.3 antibody is the most effective anti-angiogenic molecule to use in vivo.

As a conclusion, it was shown that both recombinant antibodies had an antagonist effect on VEGF activity and they were accepted as angiogenesis inhibitors.

EXAMPLES

Examples section includes the generation of recombinant antibody structure, expression, quatitatif control and examination the effects of antibody structures on cell proliferation in order to help to understand the invention. Examples includes conventional (known) methods used during the invention like agarose gel electrophoresis, polyacrylamide gel electrophoresis, transfer of genes into vector, transferring of recombinant vector into a host bacteria. These methods have been described in various publications (Samsbrook, J., Fritsch, E. F and Maniatis, T. (1989) Molecular Cloning: 2nd edition, Cold Spring Harbor Laboratory Press) and for this purpose it will not be described in the examples section.

Immunization

For the immunization studies 7-week old 3 male Balb/cJ mice were used. The first injection was done by injecting 300 µl of solution containing 150 µl of PBS and 150 µl of Freund's complete adjuvant containing 10 µg sKDR1-7 (Recombinant Human (sVEGFR2) sKDR D1-7, Research Diagnostics Inc.) under the arm pit skin of each mouse. The third week following the first immunization same amount of mixture was prepared and injected into mice by using the Freund's incomplete adjuvant. After 1-month rest period following the second immunization two mice were subjected to injection with 150 µl PBS solution containing 10 µg sKDRD1-7 from the tail vein. After four days spleen of these mice were taken to obtain total RNA.

RNA Isolation

EZ-RNA Total RNA Isolation Kit (Biological Industries, Israel) was used for the isolation of total RNA from spleen. Spleens of mice were homogenized (Janke & Kunkel Ika Werk RW20) in 1 ml "Denaturing Solution". After incubation of homogenized tissues at room temperature for 5 minutes, 1 ml "Extraction Solution" was added and samples were mixed thoroughly for 15 seconds. After this period samples were incubated for 10 minutes at room temperature and then they were centrifuged for 15 minutes at 12000 g, +4° C. After centrifugation supernatants were transferred to a new tube and 1 ml isopropanol (Merck) was added and the samples were mixed. After incubation of samples at room temperature for 10 minutes, the samples were centrifuged for 8 minutes at 12000 g, +4° C. Supernatant was removed and RNA pellets were washed with 2 ml of %75 ethanol (Merck, Katalog number 1009862500) by vortexing. RNA containing tubes were centrifuged at 7500 g, +4° C. for 5 minutes and pellets were left to dry at room temperature. After adding 100 µl DEPC threated $dH_2O$, tube were incubated at 55° C. for 15 minutes to dissolve the RNA.

VH and VL LIBRARY CONSTRUCTION

After immunization with target molecule, $sKDR_{1-7}$, Balbc/J mice spleens were taken and total RNA isolation was carried out. RNAs were checked spectrophotometrically and the $OD_{260}/OD_{280}$ ratio was calculated as 1.9. Hexamer primer based standard method (Samsbrook, Cold Spring Harbor Laboratory Press 1989, second edition) was used to create cDNA from obtained total RNA. Produced cDNA was used as template for the amplification of immunoglobulin heavy (VH, 340 bp) and light (VL, 325 bp) chain variable regions by PCR.

Heavy chain ($V_H$) variable region amplification was performed in 50 µl total volume containing 5 µl Taq polymerase buffer (10×); 3 µl $MgCl_2$ (25 mM); 1 µl of dNTP/10 mM of each, 1 µl of heavy chain primer 1 (Amersham Pharmacia, 27-1586-01), 1 µl of heavy chain primer 2 (Amersham Pharmacia, 27-1586-01), 2 µl of template cDNA, 1 µl of Taq polymerase enzyme (1 U/µl) (Fermentas).

Light chain ($V_L$) variable region amplification was performed in 50 µl total volume which contains 5 µl Taq polymerase buffer (10×); 3 µl of $MgCl_2$ (25 mM); 1 µl of dNTP/10 mM of each, 1 µl of light chain primer mix (Amersham Pharmacia, 27-1583-01), 2 µl of template cDNA, 1 µl of Taq polymerase enzyme (1 U/µl) (Fermentas).

The PCR program for the amplifications of heavy chain ($V_H$) and light chain ($V_L$) variable region was set to 5 minutes of incubation at 94° C. and 30 cycles, each cycle corresponding to 1 mM at 94° C., 2 minutes at 55° C. and 2 minutes at 72° C. PCR reaction was completed by incubating at 72° C. for 10 minutes. PCR products were checked on 1.5% agarose gel. DNA degradadation or DNA breaks were analyzed with Bio-Rad Gel Doc 2000 imaging system (FIG. 1).

Single Chain Variable Fragment (scFv) Library Construction

To obtain, Band isolations from agarose gel were made by using "Roche Agarose Gel DNA Extraction" Kit (ROCHE AGAROSE GEL DNA Extraction KIT, CATALOG NO: 1 696 505) for the obtention of 340 bp $V_H$ and 325 bp $V_L$ pure PCR products. Construction of single-chain variable fragment (scFv) was carried out at two-stage PCR reaction.

The first stage, performed in total 50 µl reaction mixture which contains 5 µl of Taq polymerase buffer (10×); 3 µl of $MgCl_2$ (25 mM); 1 µl of dNTP/10 mM from each, 3 µl $V_H$ PCR product (100 ng/µl), 3 µl $V_L$ PCR product (100 µg/µl), 4 µl linker primer (Amersham Pharmacia, 27-1588-01), 1 µl of Taq polymerase enzyme (1 U/µl) (Fermentas). Tubes containing the reaction mixture was put into Biometra Trioblock Thermoblock device and a reaction programe of 7 cycles with (94° C., 1 min, 63° C., 4 min.) was applied. At the second stage, 50 µl of mixture (34 µl $dH_2O$, 5 µl Taq polymerase buffer (10×), 3 µl $MgCl_2$ (25 mM), 1 µl dNTP/10 mM from each, 4 µl RS primer mixture (Amersham Pharmacia, 27-1589-01), 1 µl of Taq polymerase enzyme (1 U/µl), (Fermentas)) was added to the reaction mixture at the end of the seven cycles. Then a reaction programe of 25 cycles (94° C. for 1 min., 55° C. for 2 min., 72° C. for 2 min.) was applied. ScFv PCR products were controlled in 1.2% agarose gel (FIG. 2). ScFv structures and pDUCK vectors were digested with SfiI and NotI respectively and then ligated to each other.

After ligation, ligation product were incubated at 70° C., for 10 minutes and transferred into *E. Coli* TG1 bacteria.

Infective Phage Production

Bacteria containing scFv library were inoculated into 5 ml of LB medium (for 1 liter 2XTY: 10 g Bacto-Tryptone, 5 g Yeast Extract, 10 g NaCl) and incubated overnight at 37° C. and 220 rpm (incubator shaker, Innova). The next day, the overnight cultures were inoculated into 50 ml of 2XTY/Amp medium by a dilution factor of 1:100 and culture were incubated until $OD_{600}$ value reaches 0.5, at 37° C. and 220 rpm (incubator shaker, Innova). When culture $OD_{600}$ value reached 0.5, 10 ml of the bacterial cultures were transferred into new 50 ml 2XTY/Amp medium containing $10^{11}$ cfu M13K07 helper phages and culture were incubated 45 minutes at 37° C. without shaking then 45 minutes with shaking at 220 rpm at 37° C. After incubation bacterial cultures were centrifuged at room temperature at 3000 g (Sorvall RC5C+) for 10 minutes and supernatants were discarded. Pellets were resuspended in 30 ml 2XTY/Amp/Kan medium (for 1 liter of 2XTY: 100 mg of ampicilin and 50 mg of kanamycin) and incubated overnight at 37° C. at 220 rpm. The next day bacterial cultures were centrifuged at 7000 g (refrigerated centrifuge, Sorvall RC5C+) for 10 minutes at 4° C. The supernatants were then transferred into a new centrifuge tube and centrifuge again in the same conditions. 20 ml of the supernatants were transferred into a new centrifuge tube and 5 ml of PEG/NaCl (20% (w/v) polyethylene glycol 6000, 2.5 M NaCl) was added. The mixtures were incubated for two hours on ice for phage precipitation. Then phages were centrifuged for 45 minutes at 7000 rpm at +4° C. (refrigerated centrifuge, Sorvall RC5C) and supernatants were discarded. Pellets were solubilized with 1 ml of PBS (3.2 mM $Na_2HPO_4×2H_2O$, 1.4 mM $KH_2PO_4$, 2.7 mM KCl, 137 mM NaCl) and transferred into sterile microcentrifuge tubes. The suspensions were mixed with 250 µl of PEG/NaCl (20% (w/v) polyethylene glycol 6000, 2.5 M NaCl) then incubated for 30 minutes on ice. The suspensions were centrifuged for 20 minutes at 7000 rpm at +4° C. (Microsantrifuge, Eppendorf, 5415C) and supernatants were discarded. Pellets were solubilized with 200 µl of PBS (3.2 mM $Na_2HPO_4×2H_2O$, 1.4 mM $KH_2PO_4$, 2.7 mM KCl, 137 mM NaCl) and phage titration was performed for the determination of phages amount.

Phage Titration

For phage titration first minimal plates were prepared. For 100 ml of minimal medium: 50 ml of 2×M9 medium (12 g $Na_2HPO_4.2H_2O$, 6 g $KH_2PO_4$, 1 g NaCl, 2 g $NH_4Cl$ completed to 1 liter and autoclaved for 20 minutes at 121° C.) was mixed with 50 ml melted 3% agar, 200 µl 1M $MgSO_4$ and 10 µl 1M $CaCl_2$. When the mixture was cooled 2 ml of filter sterilized (0.22 µm TPP, cat no: 99522) glucose (20%) and 100 µl of filter sterilized (0.22 µm TPP, cat no: 99522) thiamine (Sigma T 4625; 10 mg/ml) was added and the medium was plated on petri dishes. F' male bacteria (*E. coli* TG1) was spread on plates containing minimal medium and incubated overnight at 37° C. The next day, one F' male bacteria (*E. coli* TG1) colony was picked and inoculated into LB medium (for 1 liter: 10 g Bacto-Tryptone (BD, cat no: 21705), 5 g Yeast Extract (BD, cat no 211929), 10 g NaCl (Applichem, cat no: A2942). The bacterias were incubated in an incubator shaker (Innova, 4230) at 37° C. until $OD_{600}$ value reaches 0.5 (Smart Spec™ 3000 BioRad). During the waiting step, appropriate phages dilutions ($10^{-2}$; $10^{-4}$; $10^{-6}$; $10^{-8}$ $10^{-10}$) were prepared with PBS (8 mM $Na_2HPO_4$, 1 mM $KH_2PO_4$, 2.7 mM KCl and 137 mM NaCl). When $OD_{600}$ value of bacteria reached 0.5 (Smart Spec™ 3000 BioRad), 100 µl of bacteria culture was transferred into sterile microsantrifuge tubes. 10 µl of each diluted phages were mixed with bacteria and incubated for 30 minutes at 37° C. At the end of incubation, infected bacteria were spread on LB/Amp plates (1 liter of melted LB/agar mixed with 100 mg Ampicilin) and the plates were placed upside-down in the incubator (Nuve EN500) at 37° C. overnight. The next day the number of formed bacterial colonies were counted and the phage concentration of the stock solution was determined.

Selection of Recombinant Phages that were Specific to KDR with BIOPANNING

Selection of VEGFR-2 binding recombinant antibodies was done according to Smith et al. 1993 (Smith, G. P., and Scott, J. K. 1993, Libraries of peptides and proteins displayed on fiamentous phage. In methods in Enzymology 217:228-257).

In this work 500 µl of coating solution (0.1 M $NaHCO_3$, pH 8.6) containing 250 ng of $sKDR_{1-7}$ was coated in biopanning tube (75 mm×12 mm immunotubes, Nunc, Maxisorb). The day after, coating solution was discarded and immunotube was blocked with blocking buffer (PBS+1% BSA) for one hour. At the end of incubation, the immunotube was washed 6 times with TPBS (PBS+0.1% [v/v] Tween-20) solution. Then $10^{11}$ cfu of phage displayed scFv library in 500 µl of TPBS (PBS+0.1% [v/v] Tween-20) was added. After 2 hours of incubation at room temperature, non-binding phages were discarded by washing 30 times with TPBS (PBS+0.1% [v/v] Tween-20) and then 30 times with PBS. After the washing step, phages bound to the target molecule were eluted by adding 500 µl of elution solution (Glycine (0.2 M pH:2.2), 1 mg/ml BSA) (Roche, cat no: 735086). The elution solution containing phages was neutralized with 75 µl of 1M Tris-HCl (pH 9.1). The amount of eluted phages was obtained by the titration of 1 µl, 10 µl and 1/10 µl of eluted phages. The remaining phages were amplified for the second biopanning step (Table 1).

No increase of sKDR binding phages was observed after the second biopanning step but an enrichment was observed after the third step. After the elution step of the third biopanning, *E. coli* TG1 bacteria were incubated for 30 min at 37° C. and the bacteria were plateted on LB/Amp/Agar plates. The next day the presence of scFv gene in bacteria colonies was controlled by colony PCR method.

Colony PCR

The presence of scFv gene in bacteria colonies was controlled by colony PCR method. Bacteria picked from colonies were solubilized in 15 µl distilled water containing 0.5 ml Eppendorf centrifuge tubes. Tubes were incubated at 95° C. for 3 minutes and centrifugated, the upper fluid was used as template for polymerase chain reaction. Primer 458: 5' ttt tgt cgt ctt tcc aga cgt t 3' and primer 459: 5' tat gac cat gat tac gcc aag 3' were used respectively as forward and reverse primers.

The PCR programe was set as 5 min at 94° C.; then 30 cycles of 1 min at 94° C., 2 min at 55° C., 2 min at 72° C. and then an elongation step of 10 min at 72° C. After PCR, products were cheeked in 1.2% in agarose gel (FIGS. 3 and 4) and two scFv clones (KDR1.3 and KDR2.6) were identified. The difference between the two clones were checked by DNA fingerprinting by digesting the scFVs PCR products with Bstn I enzyme and a DNA fingerprint study was conducted (FIG. 5).

Selecting Phage Displayed Recombinant Antibodies Able to Bind to VEGFR-2 by Phage ELISA Method To identify the binding properties of KDR1.3 and KDR2.6 that were identified as two different clones phage-ELISA was performed. To obtain phages that display KDR 1.3 and KDR 2.6, bacteria containing the scFv genes were used to generate infective phages. Infective phages were used in phage ELISA test. Each well of a 96 well ELISA plate (Falcon, cat no: 353912) was coated with 100 µl of coating buffer (0.1M $NaHCO_3$ pH: 8.6) containing 500 ngl of sKDR1-7 at +4° C. overnight. The next day wells were washed three times with 200 µl of TPBS ((%0.1 Tween 20, containing PBS (3.2 mM $Na_2HPO_4 \times 2H_2O$, 1.4 mM $KH_2PO_4$, 2.7 mM KCl, 137 mM NaCl; pH7.4)), 200 µl of blocking buffer (1% BSA+TPBS) was added into the wells and the plate was incubated for 1 hour at room temperature. Wells were then washed three times with TPBS and 100 µl of blocking buffer (PBS+%2 fat free milk)) containing phages that displaying VEGFR-2 specific recombinant antibodies ($10^{11}$ pfu) were added and incubated for 2 hours at room temperature. After incubation, wells were washed six times with TPBS, then 100 µl of blocking buffer containing 1:1000 diluted anti-M13 Horse Radish Peroxidase conjugated antibodies (Pharmacia) was added into each well. After 1 hour of incubation at room temperature wells were washed six times with TPBS. 100 µl of ABTS (Pharmacia Biotech, cat no 27-9402-01) substrate solution was added to each well for enzymatic detection. After 1 hour of incubation at room temperature, $OD_{405}$ value was read for each well with the ELISA reader (Bio-Tech ELISA Reader).

Sequence Analysis of Recombinant Antibodies

DNA sequencing reactions for KDR 1.3 and 2.6 scFVs were done according to the Beckman coulter GenomeLab Methods Development kit (608000) protocol. Primers 459 and 458 were used respectively for forward and reverse readings. Sequencing reactions were analyzed with CEQ 8800 Dye Terminator cycle sequencing automated sequencing systems CEQ8800.

DNA sequences belonging to KDR 1.3 and 2.6 clones were compared to each other with Workbench "CLUSTALW-Multiple Sequence Aligment" program (http://workbench.sdsc.edu) and sequence differences confirmed the Bstn I enzyme digestion results. The DNA sequences of KDR1.3 and KDR 2.6 are given in FIG. 6 and FIG. 7. According to the sequencing results KDR1.3 and KDR2.6 scFvs are 747 bp and 762 bp long, respectively.

Production of scFv's in Bacteria, Renaturation of Expressed scFv, Folding and Purification Production of Recombinant Antibodies in *E. coli* Cells To produce the recombinant antibodies, each *E. coli* HB2151 strain containing the KDR1.3 or 2.6 scfv clones in pDUCK phagemid vector were inoculated in 50 ml 2×YT containing 100 µg/ml of ampicillin and were allowed to grow overnight at 30° C. The next day, overnight cultures were inoculated ($OD_{600}$ 0.05) into fresh 500 ml 2×YT medium containing 100 µg/ml of ampicillin and 2% glucose. Cultures were grown at 37° C., at 250 rpm until $OD_{600}$ reached 0.5-0.6. Then bacteria were centrifuged at 3500 rpm for 10 minutes at room temperature. Resulting pellets were dissolved in 500 ml of fresh 2XTY medium containing 1 mM IPTG (Isopropyl β-D-1-thiogalactopyranoside) and ampicillin (100 ng/ml) and allowed to grow for another 4 h at 30° C. at 250 rpm (SANCHEZ L, et al. J Biotechnol., 72 (1-2), 13-20, (1999). The cultures were centrifuge at 4000 rpm for 10 min. and the supernatants were discarded. To control the ScFv production, samples taken just before induction ($T_0$) and after 4 hours of induction ($T_4$) were loaded on SDS-PAGE.

Purification of Recombinant Antibody Structures from Bacterial Cultures

After induction, periplasmic extraction was made for protein purification (Sanchez, 1999). Bacterial pellets were resuspended in 5.3 ml of TES (Tris-HCl and EDTA) and incubated on ice for 5 min. Then 6 ml of ⅓ dilution of periplasmic extraction buffer was added and the bacteria were incubated on ice for 20 min with occasional shaking. The cell extract was centrifuged at 14000 rpm for 10 min at +4° C. Because no scFv was observed in the supernatant, the pellet was subjected to an inclusion body extraction protocol (DAS, 2004). First the pellet was dissolved in 5 ml of lysis buffer (50 mM Tris pH 8.0, 200 mM NaCl, 1 mM EDTA) containing 0.2 mg/ml of lysozyme and incubated for 30 min on ice. The suspension was subjected to sonication 6 times for 10 seconds on ice. Then the bacterial suspension was centrifuged at 12,000 rpm for 15 min at +4° C. The 1th supernatant was stored at +4° C. The pellet was resuspended in 12 ml of lysis buffer containing 0.2 mg/ml lysozyme. After 15 minutes of incubated at room temperature, a second sonication was made (6 times 10 seconds). The bacterial suspension was centrifuged for 30 minutes at 12000 rpm, at +4° C. The second supernatant was stored at 4° C.

The pellet was resuspended in 12 ml lysis buffer and incubated at room temperature for 15 minutes. Then the bacterial suspension was sonicated 6 times for 10 seconds each times. After sonication SDS was added to a final concentration of 1% and the suspension was incubated for 30 minutes at room temperature then centrifuged for 30 minutes at 12000 rpm at +4° C. Third supernatant was stored at +4° C. The pellet was resuspended in 12 ml lysis buffer and was centrifuged for 20 min. at 12000 rpm at +4° C. The fourth supernatant was stored at +4° C. The pellet was resuspended in 50 mM Tris buffer pH 8.0 containing 6M urea and incubated for 45 minutes on ice. Then the sample was centrifuged at 12000 rpm for 30 minutes (DASA D., et al. 2004, J Virol Methods, 117 (2), 169-77).

All the supernatants obtained during this purification process were controlled by SDS PAGE and western blot analysis. The SDS-PAGE and western blot analysis results of KDR1.3 scFv and KDR2.6 are shown in FIG. 8 and FIG. 9, respectively.

The sixth supernatant was containing the most purified scFvs for both clones (KDR1.3 and KDR2.6), thus these supernatants were chosen for further purification steps. These supernatants were dialysed against refolding buffer containing L-arginine for two nights at +4° C. The supernatants were then dialysed for another two nights against sonication buffer. After dialysis, sample purification was carried out with metal affinity column (TALON-BD Bioscience). For this study, the resin was centrifuged at 1300 rpm for 5 minutes in 50 ml tube and the supernatant was removed. The resin was equilibrated with 10 resin volume of sonication buffer and was centrifuged at 1300 rpm for 3 minutes at room temperature. The supernatant was discarded and dialyzed samples were added in the tubes. The mixture was incubated for 30 min and then satrifuged at 1300 rpm for 5 minutes at room temperature. The supernatant was discarded and resin was washed two times with 10 resin volume resin of sonication buffer for 10 minutes. Then the resin was resuspended with one volume of sonication buffer and the suspension was transferred to an end cap column. After the decantation of the resin, the column was washed 3 times with 1 resin volume of sonication buffer. Then the recombinant antibodies were eluted from column with five resine volume of 1× elution buffer. Eluted samples were analyzed by SDS-PAGE and western blot. The TALON purification results of KDR1.3 and KDR2.6 clones were shown in FIG. 10 and FIG. 11.

Lig7 recombinant antibodies developed against the hepatitis B virus surface antigen was used as negative control for the analysis of the effects of KDR 1.3 and 2.6 recombinant antibodies on VEGF related HUVE cell proliferation assays.

Second elution tubes of TALON purified KDR 1.3 and 2.6 scFvs and Lig7 elution samples were dialysed against PBS overnight and used in cell culture assays and after filter sterilization. The scFv concentrations were determined with BCA method (Pierce 23225).

After the induction of process of recombinant antibodies in 500 ml of media 500 μl of TALON purified scFvs were obtained. The amount of purified KDR 1.3 scFv was changing between 85 ng/μl to 156 ng/μ with an average of 120 ng/μ and for KDR2.6 the amount of scFv was changing between 88 ng/μl to 125 ng/μl with an average of 105 ng/μl. Differences between the amount of recombinant antibody purification products and the activity may arise from the differences in folding of the antibody structure during the purification steps (Wulfing, C. And Plunckthun, A., 1994, J. Mol. Biol., 242, 655-669); Dasa D., et al. 2004, J Virol Methods, 117 (2), 169-77). These folding variations may be due to the differences in sequences which might also interfere with the host cell genetic stability (Knappik, A., et al. 1993, Bio/Technology, 11, 77-83).

Determination of the Binding Properties of Soluble KDR1.3 and KDR2.6 scFv to Soluble KDR by ELISA The binding property of the KDR1.3 and KDR 2.6 scFvs was determined by ELISA method. Each well of ELISA well plate were coated with 100 μl target antigen (0.5 μg) at +4° C. overnight. The next day the wells were washed three times with 200 μl of TPBS (%0.1 Tween 20 containing PBS) and then blocked with 200 μl of blocking buffer (PBS+%1 BSA) for 1 hour at room temperature. Wells were washed three times with TPBS, then 100 μl of blocking buffer containing anti KDR recombinant antibodies (~1 μg) or no recombinant antibody, as negative control, was added to wells and incubated at room temperature for 2 hours. After incubation wells were washed six times with TPBS, then 100 μl of blocking buffer containing 1:5000 anti-Myc tag Horse Radish Peroxidase conjugated antibodies (Sigma) was added into each well and incubated at room temperature for 1 hour. After washing 6 times with TPBS, 100 μl of ABTS substrate solution (Pharmacia Biotech, cat no 27-9402-01) was added to each well. After one hour of incubation at room temperature, the $OD_{405}$ value for each well was detected with the ELISA reader (Bio-Tech ELISA Reader). ELISA results were given in FIG. 12. While the $OD_{405}$ value for negative controls were around 0.09, the $OD_{405}$ value for the second elution tubes for KDR 1.3, KDR 2.6 and Lig7 was 0.250, and 0.512 and 0.605. So solubly expressed KDR 1.3 and KDR 2.6 scFv's were still binding to KDR and could be used for cell culture experiments.

Human Umbilical Vein Endothelial Cells (HUVEC) Isolation and In Vitro Culture

The expected properties of recombinant antibodies obtained according to the description cited above is the inhibition of cell proliferation by blocking the activity of VEGFR-2. For this purpose for determining the concentration of recombinant antibody necessary for the inhibition of HUVEC proliferation and the percentage of inhibition in vitro cell proliferation assay was done.

HUVE Cells were purified and cultured using a modification of the procedure described by Jaffe et al. (Jaffe et al. *J Clin Invest.* 1973; 52:2745-56). Cells were maintained in M199 endothelial cell growth medium (Biological Industries, Israel), containing 20% fetal bovine serum, 20 mM HEPES pH:7.4, penicillin (100 µg/mL), streptomycin (100 µg/mL) and heparin (5 µ/mL) in tissue-culture plates coated with human plasma fibronectin (40 µg/ml).

HUVEC BRDU Proliferation Assay

For the detection of the KDR blocking activity of the recombinant antibodies on cell proliferation a kit allowing the measurement of the incorporation of an nucleotide analogue (BrdU) into replicating DNA was used.

For this purpose Roche BRDU kit was used (Roche, Kat. No. 1444611). BrdU is a nucleotide analogous which integrates into the replicating DNA during cell division. Then the uptake of BrdU into cells was measured by fluorescent markers conjugated anti-BrdU antibodies.

For the BRDU assay HUVE Cells were plated onto 96-well tissue culture plates and cultivated as mentioned above. For the experiments HUVE Cells were seeded at a density of 5000 cells/well in 96-well tissue culture plates coated with 1% gelatin. After allowing the cells to attach for 3 h, the medium was replaced with M199 medium containing 2% FBS and cells were cultivated for 16 h.

Antibodies were diluted in a medium containing 5 or 10 ng/ml of VEGF at room temperature and these freshly prepared antibody dilutions were added each day to the cell culture for two days.

16 Hours before the end of the experiment, BrdU was added to the cells to a final concentration of 10 µM. At the end of the experiment, cells were washed and fixed. BrdU labeling was done according to the manufacturer's instructions. The amount of BrdU incorporation in each well was determined by spectrophotometric reading at 405 nm. The absorbance value at 490 nm was subtracted from the absorbance value at 405 nm for each sample.

In the next experiments, the effect of different KDR1.3 and KDR2.6 recombinant antibodies concentrations at different times on HUVE Cell proliferation was analyzed (FIG. 13). The percentage of inhibition of HUVE Cell proliferation for a concentration of 1 µg/ml of recombinant antibodies was calculated according to the average of four different proliferation assays.

Ab 293: % 84±20.1
KDR 1.3: % 60±23.7
KDR 2.6: % 40±17.4

Investigation of In Vivo Anti-Angiogenic Effects of Recombinant Soluble Antibodies in the Cornea Angiogenesis Model Arteriovenous Malformation (AVM) tissues used in the cornea angiogenesis model, has been obtained by the surgery in Marmara University, Neurological Sciences Institute and KDR1.3, KDR2.6 and Lig-7 recombinant antibodies were tested in these models.

Cornea Angiogenesis Model

Cornea is an avascular tissue, which normally does not include blood vessels. When an angiogenically active tissue is placed in micropocket on the surface of cornea, vascularization of the cornea starts at the 3rd or 4th weeks. This feature of the cornea maintains an avenue to study in vivo angiogenesis (Barbel M et al, *Inv. Ophthalmology & Vis. Sci.*, 1996, Vol: 37, No: 8 p. 1625-1632). Each tissue samples (AVMs in liquid nitrogen at 187° C.) to be inoculated in to cornea, was brought to room temperature, washed with dimethylsulfoxide, and cut into suitable-sized (approximately 2- to 3-mm diameter) pieces under the microscope.

10 Sprague-Dawley rats were used in this study. One of rats was removed from the study because of the infection. The steps in the procedure for corneal implantation are done by following the previously published literature (Polverini P J, et al, *Lab. Invest.*, 1984, 51, 635-642), and are shown in FIG. 14. Each rat was anesthetized with an intraperitoneal injection of ketamine, and all manipulations were performed under the microscope under sterile conditions. Both corneas of each animal were anesthetized with topical 0.5% propacaine, and each globe was gently proptosed with jeweler's forceps. Under an operating microscope, a paracentral intrastromal linear kera-totomy (approximately 4 mm long and at a right angle to the limbus) was performed with an arachnoid blade. Then, a micro-hook was used to form a micropocket in the corneal tissue. A uniform amount of tissue was implanted in the micropocket between the two epithelial layers of the cornea. The date the procedure was performed was taken as Day 0.

Figure 16:
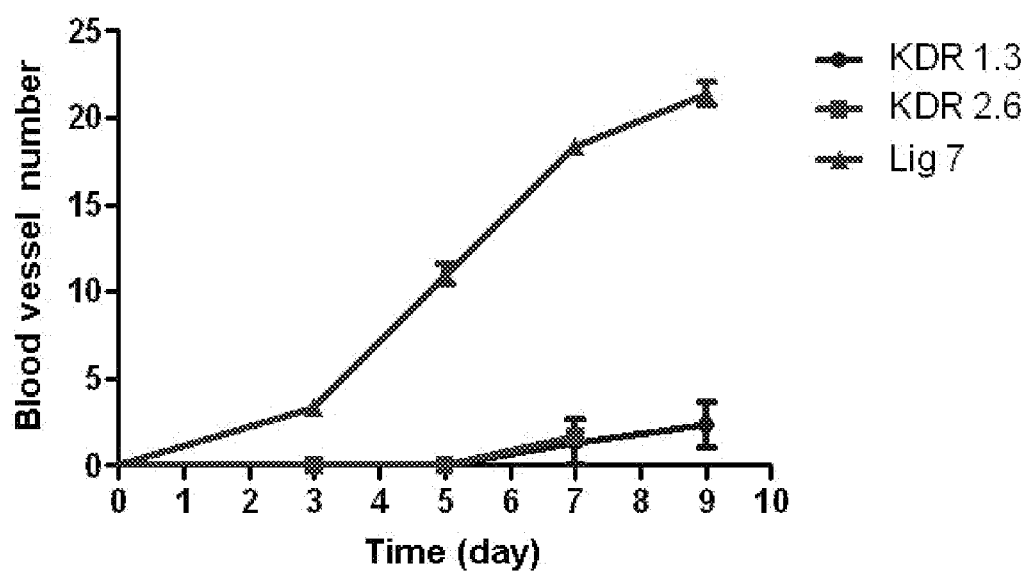
FIG. 16: Difference between the anti-angiogenic effectiveness of antibodies. Number of blood vessel formed during the experiment on angiogenesis inhibitory effect of the recombinant antibodies on arteriovenus malformation tissue grafted in rat cornea at day 3, 5, 7 and 9.

The Study of the Anti-Angiogenic Effects of Recombinant Antibodies in Rat Cornea Angiogenesis Assay Sprague-Dawley rats weighing 300 to 400 grams were used all experiments. Nine rats were used for the corneal angiogenesis assay. KDR1.3, KDR 2.6 and Lig-7 antibodies (200 µl, 25 ng/µl) were intravenously injected every day at the same time in rats bearing AVM in the cornea and the groups were followed during 10 days. In the study were Lig-7 was used as negative control each cornea was photographed at 3rd, 5th, 7th and 9th days and newly formed blood vessels have been counted for the evaluation (FIG. 15). The rat corneas observed during 10 days were photographed and the pictures were shown FIG. 16. When the group where KDR1.3 was used, was compared with the control group, regression of vascularization was visualized. Vascularization regression was also visualized in the KDR 2.6 group but rat deaths occurred in the $9^{th}$ day due to weakening.

Angiogenic activity measurement was done for KDR 1.3, KDR 2.6 and the control groups and then General Linear Mode (GLM), Univariate variation analysis test was performed with SPSS version 15.0 for comparing statistically the vessel numbers at the 3rd, 5th, 7th and 9th days and Tukey HSD and Student-Newman-Keuls tests were used for Post-hoc comparison. Statistical evaluations revealed that the anti-angiogenic activities of KDR 1.3 and KDR 2.6 antibodies were statistically significant (KDR 1.3; $p<0.05$ and KDR 2.6; $p<0.05$). But rat deaths occurred when KDR 2.6 antibodies was used. The in vivo experiments showed that KDR 1.3 antibody is the most effective anti-angiogenic molecule to use in vivo.

The blocking ability of the two recombinant antibodies (KDR1.3 and KDR2.6) mentioned is this patent on HUVE Cells proliferation and their anti-angiogenic effects on rat cornea in vivo model was demonstrated. In year 1998, Zhu et al. produced a scFv (p1C11) against KDR with 2.1 nM affinity by immunizing mice with KDR-AP and obtained an inhibition of 48% on HUVE Cell proliferation with 1 µg/ml concentration of KDR (Zhu et al, 1998, *Cancer Res.* 58, 3209-3214). Furthermore a rat monoclonal antibody developed against Flk1 showed an inhibition effect of 25% on G55 cells (Kunkel P ve ark. 2001, *Cancer Research* 61, 6624-6628). A monoclonal antibody (YcomB3) developed against KDR Ig domain III showed an inhibition effect of 50% on HUVE cells at 0.5 mg/L of concentration and this antibody was proposed as a candidates for antianjiogenik applications (Li R et al. 2004; *Acta Pharmacol Sin* 25 (10): 1292-1298).

There are studies on increasing affinities of antibody structures. In 1996, Davies and Riechmann have shown that a mutation on the heavy chain variable region was involved in the CDR1 affinity. The antibody affinity was decreased to 25 nM from 160 nM (Daves and Rechmann, 1996 Immunotechnology, 2, 169-79, (1996). Lippow et al. in 2007, showed that changing 4 amino acids in light chain reagion of an antibody against lysosyme, increased the affinity 140 times (30 pM) (Lippow S. M et al. 2007, Nat. Biotechnol., 25, 1171-1176). Today, Ranibizumab which is used against for inhibiting angiogenesis is a derivative of Bevacizumab by 5 amino acid changes in the variable region and by 1 residue in the constant region. These changes have increased hundred times the affinity of the antibody against the VEGF (192 pM). In summary, the affinity of KDR1.3 and 2.6 recombinant antibody structures and thereby their antiangiogenic properties can be increased by modifying their sequences.

The invention claimed is:

1. An anti-VEGF receptor-2 recombinant antibody, which is a single chain Fv (scFv), comprising:
   a Variable Heavy Chain (VH) comprising an amino acid sequence of SEQ ID NO:7; and
   a Variable Light Chain (VL) comprising an amino acid sequence of SEQ ID NO: 8,
   wherein the anti-VEGF receptor-2 recombinant antibody shows a statistically significant blood vessel inhibition in arteriovenus malformation tissue grafted rat cornea assay following 7 days of treatment.

2. A DNA molecule encoding the recombinant antibody of claim 1 comprising:
   a Variable Heavy Chain (VH) comprising a nucleic acid sequence of SEQ ID NO:15; and
   a Variable Light Chain (VL) comprising a nucleic acid sequence of SEQ ID NO:16.

3. A recombinant vector comprising the sequences defined in claim 2.

4. A pharmaceutical composition comprising the vector of claim 3 or polypeptides comprising at least one of the amino acid sequences defined in claim 1.

5. The anti-VEGF receptor-2 recombinant antibody of claim 1, wherein the antibody is labeled with a labeling agent selected from the group consisting of radioactive and fluorescent compounds, enzymes (Horse Radish Peroxidase, Alkalen Phosphatase), biotin, streptavidin, and nanoparticles (gold and magnetic particles, nanotubes, quantum dots).

6. An anti-VEGF receptor-2 recombinant antibody, which is a single chain Fv (scFv), comprising:
   a Variable Heavy Chain (VH) comprising an amino acid sequence of SEQ ID NO:23; and
   a Variable Light Chain (VL) comprising an amino acid sequence of SEQ ID NO: 24,
   wherein the anti-VEGF receptor-2 recombinant antibody shows a statistically significant blood vessel inhibition in arteriovenus malformation tissue grafted rat cornea assay following 7 days of treatment.

7. The A DNA molecule encoding the recombinant antibody of claim 6 comprising:
   a Variable Heavy Chain (VH) comprising a nucleic acid sequence of SEQ ID NO:31; and
   a Variable Light Chain (VL) comprising a nucleic acid sequence of SEQ ID NO:32.

8. A recombinant vector comprising the sequences defined in claim 7.

9. A pharmaceutical composition comprising the vector of claim 8 or polypeptides comprising the amino acid sequences defined in claim 6.

10. The anti-VEGF receptor-2 recombinant antibody of claim 6, wherein the antibody is labeled with a labeling agent selected from the group consisting of radioactive and fluorescent compounds, enzymes (Horse Radish Peroxidase, Alkalen Phosphatase), biotin, streptavidin, and nanoparticles (gold and magnetic particles, nanotubes, quantum dots).

* * * * *